United States Patent
Tamaki et al.

(10) Patent No.: US 10,500,396 B2
(45) Date of Patent: Dec. 10, 2019

(54) ELECTRICAL STIMULATION SYSTEM

(71) Applicant: H2L Inc., Tokyo (JP)

(72) Inventors: Emi Tamaki, Tokyo (JP); Kenichiro Iwasaki, Tokyo (JP)

(73) Assignee: H2L Inc., Tokyo (JP)

(*) Notice: Subject to any disclaimer, the term of this patent is extended or adjusted under 35 U.S.C. 154(b) by 0 days.

(21) Appl. No.: 16/081,849

(22) PCT Filed: Mar. 10, 2017

(86) PCT No.: PCT/JP2017/009707
§ 371 (c)(1),
(2) Date: Aug. 31, 2018

(87) PCT Pub. No.: WO2017/155085
PCT Pub. Date: Sep. 14, 2017

(65) Prior Publication Data
US 2019/0076647 A1 Mar. 14, 2019

(30) Foreign Application Priority Data
Mar. 10, 2016 (JP) .................. 2016-047583

(51) Int. Cl.
| A61N 1/00 | (2006.01) |
| A61N 1/36 | (2006.01) |
| G06N 20/00 | (2019.01) |
| A61B 5/11 | (2006.01) |
| A61B 5/00 | (2006.01) |
| G06N 7/00 | (2006.01) |

(52) U.S. Cl.
CPC .......... *A61N 1/3603* (2017.08); *A61B 5/0059* (2013.01); *A61B 5/1104* (2013.01);
(Continued)

(58) Field of Classification Search
CPC .... A61N 1/36; A61N 1/3603; A61N 1/36128; A61N 1/36139; A61N 1/36103;
(Continued)

(56) References Cited

U.S. PATENT DOCUMENTS 6,244,873 B1* 6/2001 Hill .................. G06F 3/015
379/110.01
7,184,837 B2 2/2007 Goetz
(Continued)

FOREIGN PATENT DOCUMENTS

| JP | 2014104241 A | 6/2014 |
| WO | 2011/153213 A1 | 12/2011 |
| WO | 2014/113813 A1 | 7/2014 |

OTHER PUBLICATIONS

International Search Report dated May 16, 2017 filed in PCT/JP2017/009707.
(Continued)

*Primary Examiner* — Mallika D Fairchild
(74) *Attorney, Agent, or Firm* — Rankin, Hill & Clark LLP

(57) ABSTRACT

Provided are an electrical stimulation device configured so that a correspondence among finger motion and electrodes can be clarified in a short amount of time regardless of the state of attachment to a user's arm and an individual difference and an intended finger can be driven at high accuracy with very few erroneous operation and an electrical stimulation system using the electrical stimulation device. When an electrode probability matrix in which a Bayesian posterior probability indicating an electrode-finger correspondence is described as an element is updated in a host, the position of an element positioned on the upper left side of the electrode probability matrix and indicating that finger motion occurs is compared to rearrange the columns of the electrode probability matrix as necessary.

2 Claims, 16 Drawing Sheets

(52) U.S. Cl.
CPC .......... *A61B 5/1107* (2013.01); *A61B 5/6826* (2013.01); *A61N 1/36003* (2013.01); *G06N 7/005* (2013.01); *G06N 20/00* (2019.01); *A61B 2560/0223* (2013.01); *A61B 2560/0468* (2013.01)

(58) Field of Classification Search
CPC .. A61N 1/3625; A61N 1/0484; A61N 1/0492; A61B 5/1104; A61B 5/6824; A61B 5/6825; A61B 5/6826; G06N 7/005
See application file for complete search history.

(56) References Cited

U.S. PATENT DOCUMENTS

| | | | | |
|---|---|---|---|---|
| 2004/0082979 | A1* | 4/2004 | Tong | A61N 1/0452 607/48 |
| 2004/0267331 | A1* | 12/2004 | Koeneman | A61H 1/02 607/49 |
| 2005/0006008 | A1 | 1/2005 | Cho | |
| 2011/0264002 | A1 | 10/2011 | Kolen | |
| 2012/0059298 | A1 | 3/2012 | Hoffman et al. | |
| 2015/0321000 | A1 | 11/2015 | Rosenbluth et al. | |

OTHER PUBLICATIONS

Japanese Notification of Reasons for Refusal dated Nov. 14, 2017 for the corresponding Japanese Patent Application No. 2016-047583.
Japanese Notification of Reasons for Refusal dated Feb. 6, 2018 for the corresponding Japanese Patent Application No. 2016-047583.
Decision to Grant a Patent dated Mar. 27, 2018 for the corresponding Japanese Patent Application No. 2016-047583.
Extended European Search Report (EESR) dated Oct. 16, 2019 in the corresponding European patent application No. 17763425.0.

* cited by examiner

1. THUMB-BENT
2. INDEX FINGER-BENT
3. MIDDLE FINGER-BENT
4. RING FINGER OR LITTLE FINGER-BENT
5. WRIST-PALMAR FLEXION
6. WRIST-DORSAL FLEXION
7. WRIST-RADIAL FLEXION
8. WRIST-ULNAR FLEXION

ELECTRICAL STIMULUS

| | 1 | 2 | 3 | 4 | 5 | 6 | 7 | 8 |
|---|---|---|---|---|---|---|---|---|
| | 595 | 120 | 0 | 0 | 0 | 0 | 0 | 0 |
| | 115 | 700 | 0 | 0 | 0 | 0 | 0 | 0 |
| | 92 | 115 | 225 | 0 | 0 | 0 | 0 | 0 |
| | 0 | 0 | 815 | 230 | 115 | 0 | 0 | 0 |
| | 0 | 0 | 110 | 0 | 705 | 110 | 0 | 0 |
| | 0 | 0 | 0 | 0 | 110 | 810 | 210 | 0 |
| | 0 | 0 | 0 | 0 | 0 | 215 | 0 | 0 |
| | 0 | 0 | 0 | 0 | 0 | 0 | 0 | 0 |

| 595 | 120 | 0 | 0 | 0 | 0 | 0 | 0 |
|---|---|---|---|---|---|---|---|
| 115 | 700 | 0 | 0 | 0 | 0 | 0 | 0 |
| 92 | 115 | 225 | 0 | 0 | 0 | 0 | 0 |
| 0 | 0 | 815 | 230 | 115 | 0 | 0 | 0 |
| 0 | 0 | 110 | 0 | 705 | 110 | 0 | 0 |
| 0 | 0 | 0 | 0 | 110 | 810 | 210 | 0 |
| 0 | 0 | 0 | 0 | 0 | 215 | 0 | 0 |
| 0 | 0 | 0 | 0 | 0 | 0 | 0 | 0 |

| 595 | 700 | 815 | 230 | 705 | 810 | 210 | 0 | ~1201 |
|---|---|---|---|---|---|---|---|---|
| ○ | ○ | ○ | × | ○ | ○ | × | × | ~1202 |

FIG. 12C

| ○ | × | × | × | × | × | × | × |
|---|---|---|---|---|---|---|---|
| × | ○ | × | × | × | × | × | × |
| × | × | × | × | × | × | × | × |
| × | × | ○ | × | × | × | × | × |
| × | × | × | × | ○ | × | × | × |
| × | × | × | × | × | ○ | × | × |
| × | × | × | × | × | × | × | × |
| × | × | × | × | × | × | × | × |

FIG. 12D

| 1 | 0 | 0 | 0 | 0 | 0 | 0 | 0 |
|---|---|---|---|---|---|---|---|
| 0 | 1 | 0 | 0 | 0 | 0 | 0 | 0 |
| 0 | 0 | 0 | 0 | 0 | 0 | 0 | 0 |
| 0 | 0 | 1 | 0 | 0 | 0 | 0 | 0 |
| 0 | 0 | 0 | 0 | 1 | 0 | 0 | 0 |
| 0 | 0 | 0 | 0 | 0 | 1 | 0 | 0 |
| 0 | 0 | 0 | 0 | 0 | 0 | 0 | 0 |
| 0 | 0 | 0 | 0 | 0 | 0 | 0 | 0 |

*FIG. 16A*
$$\begin{pmatrix} 0 & 595 & 120 & 0 & 0 & 0 & 0 & 0 \\ 0 & 115 & 700 & 0 & 0 & 0 & 0 & 0 \\ 0 & 92 & 115 & 225 & 0 & 0 & 0 & 0 \\ 0 & 0 & 1 & 815 & 230 & 115 & 0 & 0 \\ 0 & 0 & 0 & 110 & 0 & 705 & 0 & 110 \\ 0 & 0 & 0 & 0 & 0 & 110 & 210 & 810 \\ 0 & 0 & 0 & 0 & 0 & 0 & 0 & 215 \\ 0 & 0 & 0 & 0 & 0 & 0 & 0 & 0 \end{pmatrix}$$

*FIG. 16B*
P1601   A1602
$$\begin{pmatrix} 0 & 1 & 0 & 0 & 0 & 0 & 0 & 0 \\ 0 & 0 & 1 & 0 & 0 & 0 & 0 & 0 \\ 0 & 0 & 0 & 0 & 0 & 0 & 0 & 0 \\ 0 & 0 & 0 & 1 & 0 & 0 & 0 & 0 \\ 0 & 0 & 0 & 0 & 0 & 0 & 0 & 0 \\ 0 & 0 & 0 & 0 & 0 & 1 & 0 & 0 \\ 0 & 0 & 0 & 0 & 0 & 0 & 0 & 1 \\ 0 & 0 & 0 & 0 & 0 & 0 & 0 & 0 \end{pmatrix}$$

*FIG. 16C*
P1603  A1604                    A1605
$$\begin{pmatrix} 1 & 0 & 0 & 0 & 0 & 0 & 0 & 0 \\ 0 & 1 & 0 & 0 & 0 & 0 & 0 & 0 \\ 0 & 0 & 0 & 0 & 0 & 0 & 0 & 0 \\ 0 & 0 & 1 & 0 & 0 & 0 & 0 & 0 \\ 0 & 0 & 0 & 0 & 1 & 0 & 0 & 0 \\ 0 & 0 & 0 & 0 & 0 & 1 & 0 & 0 \\ 0 & 0 & 0 & 0 & 0 & 0 & 0 & 0 \\ 0 & 0 & 0 & 0 & 0 & 0 & 0 & 0 \end{pmatrix}$$

*FIG. 16D*
A1605  P1603  A1604
$$\begin{pmatrix} 0 & 1 & 0 & 0 & 0 & 0 & 0 & 0 \\ 0 & 0 & 1 & 0 & 0 & 0 & 0 & 0 \\ 0 & 0 & 0 & 0 & 0 & 0 & 0 & 0 \\ 0 & 0 & 0 & 1 & 0 & 0 & 0 & 0 \\ 0 & 0 & 0 & 0 & 0 & 1 & 0 & 0 \\ 0 & 0 & 0 & 0 & 0 & 0 & 1 & 0 \\ 0 & 0 & 0 & 0 & 0 & 0 & 0 & 0 \\ 0 & 0 & 0 & 0 & 0 & 0 & 0 & 0 \end{pmatrix}$$

$$\begin{pmatrix} 0 & 0.2 & 0 & 0 & \cdots & 0 \\ 0.3 & 0.85 & 0.2 & 0.01 & \cdots & 0 \\ 0.02 & 0.1 & 0.9 & 0.05 & \cdots & 0 \\ & \vdots & & \vdots & \vdots & \\ 0 & \cdots & P(x|j) & & \cdots & 0 \\ & \vdots & & \vdots & \vdots & \\ 0 & \cdots & 0 & & \cdots & 0 \end{pmatrix}$$

FIG. 17

ELECTRICAL STIMULATION SYSTEM

TECHNICAL FIELD

The present invention relates to an electrical stimulation device configured to provide an electrical stimulation signal to a muscle of an arm of a person and detect displacement of the muscle of the arm by a sensor and an electrical stimulation system having a combination of the electrical stimulation device and an information processing device.

BACKGROUND ART

Typically, an attempt has been made to move a finger or a hand of a user by a command from the outside in such a manner that multiple electrodes are attached to a forearm of a person (the user) to provide electrical stimulation signals to muscles of the forearm. For example, it has been considered that, e.g., rehabilitation, training, and motion assistance of fingers are performed by the command from the outside. Moreover, it has been also proposed that when, e.g., a head-mounted display is used to execute the virtual reality processing (Virtual Reality) of providing the user with a virtual space image or the augmented reality processing (Augmented Reality) of superimposing a virtual object image on an actual space video, fingers are moved in association with, e.g., a virtual space video based on the command from the outside to enhance reality.

The inventors of the present application have proposed an electrical stimulation device as described in advance in Patent Literature 1. The electrical stimulation device proposed in Patent Literature 1 is a device configured such that multiple electrodes are attached to a band to be attached to a forearm of a user to provide electrical stimuli to muscles of the forearm.

CITATION LIST

Patent Literature

PATENT LITERATURE 1: JP-A-2014-104241

SUMMARY OF THE INVENTION

Problems to be Solved by the Invention

The user wearing the electrical stimulation device proposed in Patent Literature 1 moves one's finger or hand by the electric stimuli provided to the muscles of the forearm according to a command from the outside. For example, the muscles of the forearm for moving five fingers by stimulation are known in advance, and the electrode attached to the electrical stimulation device is used to stimulate a specific muscle to move the finger corresponding to such a muscle.

A situation is assumed, in which the user wears a band-shaped electrical stimulation device on the forearm. In this situation, the band-shaped electrical stimulation device includes multiple electrodes, but a correspondence between the electrode and the muscle needs to be sensed. For such sensing, when the user wears the band-shaped electrical stimulation device, a calibration process needs to be first performed to output an electrical stimulation signal from each electrode and to check, in advance, which finger moves.

That is, when the user wears the band-shaped electrical stimulation device, the electrical stimulation device needs to accurately grasp, in advance, to which muscle each electrode arranged at the electrical stimulation device corresponds. For this reason, the calibration process has a significantly important meaning.

A person arm thickness greatly varies according to an individual difference such as an age, a gender, and a body weight. For this reason, for absorbing the individual difference in the arm thickness only by a single electrical stimulation device, a greater number of electrodes and sensors than the number of fingers, i.e., five fingers, needs to be provided. Accordingly, some electrodes do not correspond to finger motion. That is, for accurately operating the electrical stimulation device, the correspondence between the muscle for actually moving the finger and the electrode needs to be clarified in advance by the calibration process.

The present invention has been made in view of the above-described problems, and is intended to provide an electrical stimulation device configured so that a correspondence among finger motion and electrodes can be clarified in a short amount of time regardless of the state of attachment to a user's arm and an individual difference and an intended finger can be driven at high accuracy with very few erroneous operation and an electrical stimulation system using the electrical stimulation device.

Solution to the Problems

For solving the above-described problems, the electrical stimulation device of the present invention includes a band to be wound around an arm of a user, multiple electrodes arranged on one surface of the band, a multiplexor configured to select one of the multiple electrodes, a near field communication receiving unit configured to receive a command for moving a finger from a host, an electrode probability matrix configured such that a correspondence among finger motion and the multiple electrodes is described in terms of probability, and a finger-electrode correspondence conversion unit configured to specify, based on the command for moving the finger, an electrode with the maximum probability from the electrode probability matrix and to control the multiplexor to select the specified electrode.

Effect of the Invention

According to the present invention, the electrical stimulation device configured so that the correspondence among finger motion and the electrodes can be clarified in a short amount of time regardless of the state of attachment to the user's arm and the individual difference and the intended finger can be driven at high accuracy with very few erroneous operation and the electrical stimulation system using the electrical stimulation device can be provided.

Other problems, configurations, and advantageous effects than above will be apparent from description of an embodiment below.

BRIEF DESCRIPTION OF THE DRAWINGS

FIG. 12 is a view for describing a finger behavior matrix indicating finger motion in response to the electrical stimulus, a view of the procedure of selecting an effective electrical stimulus from the finger behavior matrix, a view for describing a flag matrix indicating a result of selection of the effective electrical stimulus from the finger behavior matrix, and a view of an electrode probability matrix generated from the flag matrix:

FIG. 16 is a view of an example of the finger behavior matrix produced in the second learning mode or later, a virtual electrode probability matrix produced based on the finger behavior matrix, an electrode probability matrix stored in the host before application of the learning mode, and rearranged rows and columns of the electrode probability matrix; and FIG. 17 is a view of one example of a generalized electrode probability matrix.

DESCRIPTION OF THE EMBODIMENTS

Figure 1:
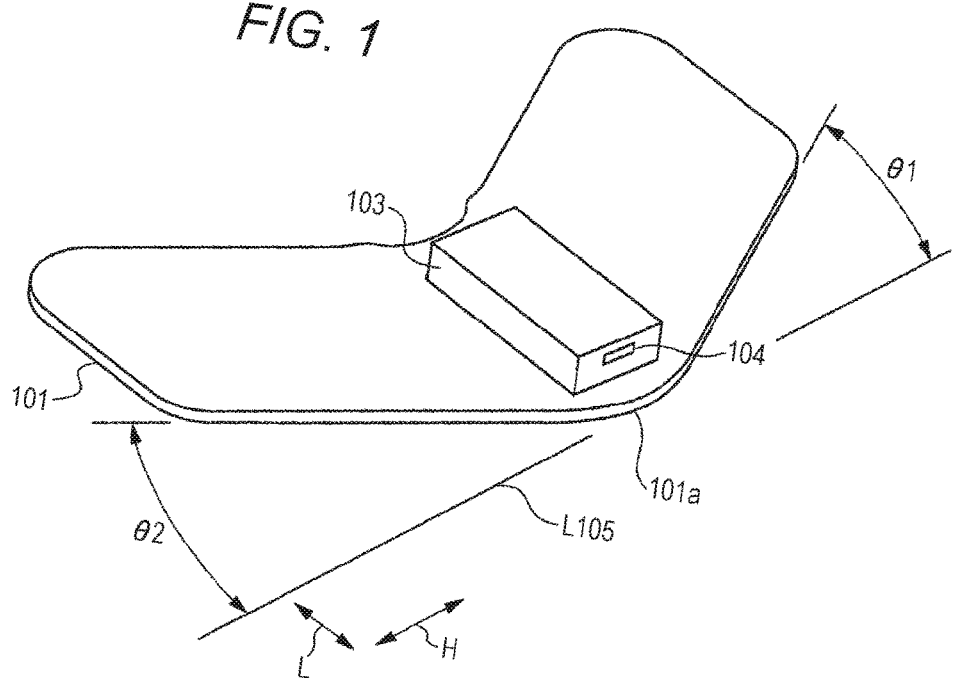
FIG. 1 is a perspective view of an outer appearance of an electrical stimulation device as an example embodiment of the present invention.

FIG. 1 is a perspective view of an outer appearance of an electrical stimulation device 100 as an example embodiment of the present invention.

The electrical stimulation device 100 includes a V-shaped band 101. The band 101 is made with, e.g., a resin sheet of silicone rubber exhibiting flexibility. Both wing portions of the band 101 are in a shape inclined at an equal inclination angle θ1, θ2 from a horizontal line L105. The inclination angles θ1, θ2 are 32°, for example. A rectangular circuit housing box 103 is provided on a front-surface-side center portion of the band 101. The circuit housing box 103 includes, for example, a later-described built-in arithmetic processing unit 150 (see FIG. 4) and a built-in secondary battery.

A first serial interface terminal 104 is provided on one short-side surface of the circuit housing box 103. The first serial interface terminal 104 is, for example, a micro USB terminal. The electrical stimulation device 100 charges the not-shown built-in secondary battery via the first serial interface terminal 104. Moreover, the first serial interface terminal 104 is connected to a personal computer etc. so that function extension such as updating of firmware as a component of the arithmetic processing unit is available.

A back surface (a lower surface in FIG. 1) of the band 101 on the opposite side of the surface to which the circuit housing box 103 is attached is an electrode arrangement surface 100a described later with reference to FIG. 2.

As described later with reference to an attachment example of FIGS. 3A and 3B, the electrical stimulation device 100 is attached to a user in such a manner that the electrode arrangement surface 100a as the back surface of the band 101 is wound around the forearm of the user.

Figure 2:
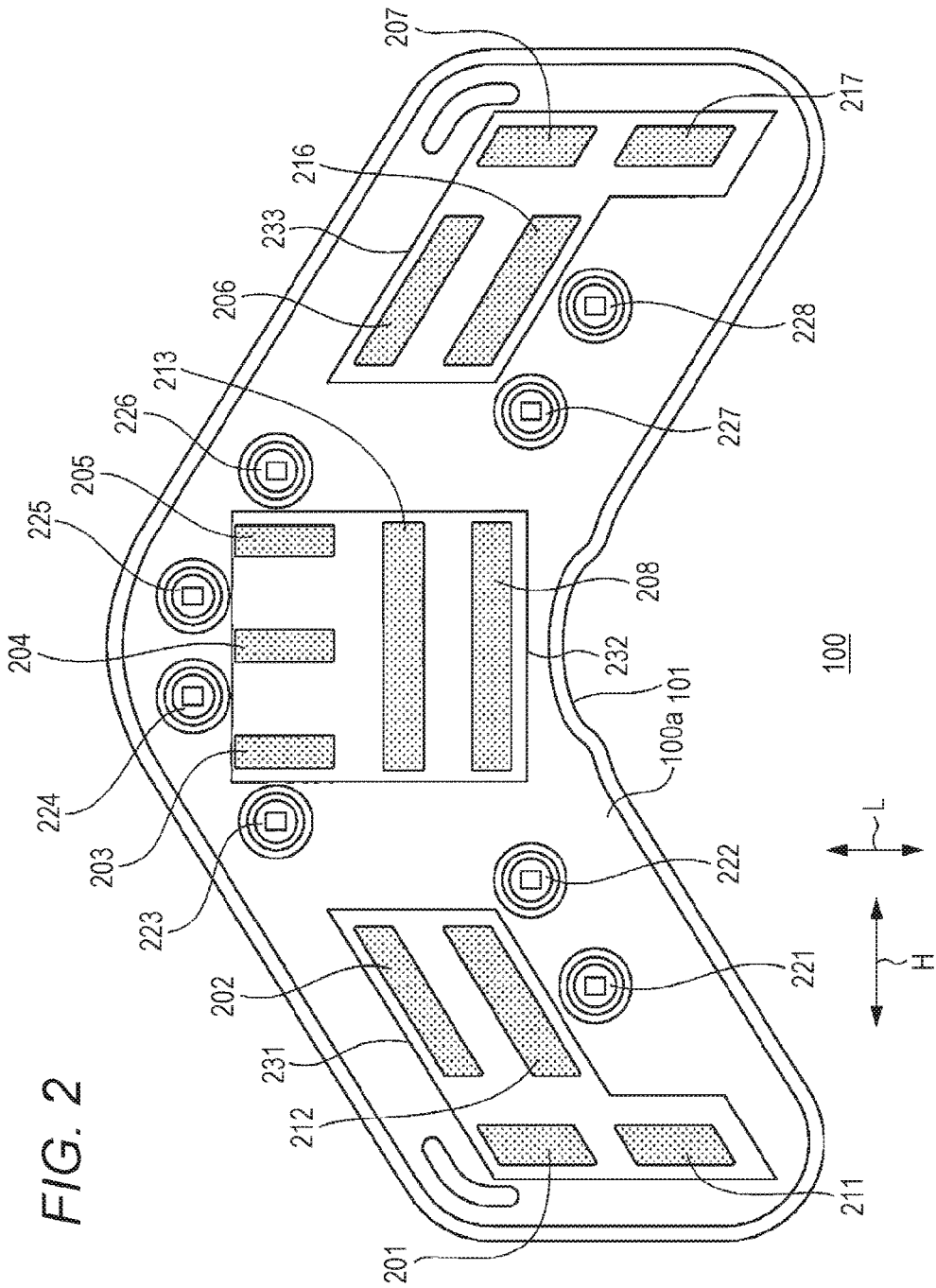
FIG. 2 is a plan view of an electrode arrangement surface.

FIG. 2 is a plan view of the electrode arrangement surface 100a.

The electrode arrangement surface 100a includes electrodes 201 to 208 configured to provide electrical stimulation signals to muscles of the forearm of the user, and electrodes 211 to 213, 216, 217 as ground electrodes paired with the electrodes 201 to 208 upon use. Note that the common ground electrode is used for multiple opposing electrodes, and therefore, the number of electrodes 201 to 208 and the number of electrodes 211 to 213, 216, 217 are not necessarily coincident with each other.

In addition, the electrode arrangement surface 100a includes muscle displacement sensors 221 to 228 configured to detect motion of the muscles of the forearm of the user.

A right electrode arrangement spot 231 is provided on the right side (on the left side in the figure) of the electrode arrangement surface 100a, and four electrodes 201, 202, 211, 212 are arranged at the right electrode arrangement spot 231. Of four electrodes 201, 202, 211, 212, the electrode 201 is a first electrode, and the electrode 202 is a second electrode. Moreover, the electrode 211 is a ground electrode facing the electrode 201, and the electrode 212 is a ground electrode facing the electrode 202.

The electrode 201 and the electrode 211 are electrodes configured to provide stimuli to the muscles of the forearm, and upon attachment, are arranged adjacent to each other in a longitudinal direction L of the arm.

The electrode 202 and the electrode 212 are also electrodes configured to provide stimuli to the muscles of the forearm, and are substantially rectangular electrodes arranged with these electrodes being inclined with respect to a circumferential direction H at the inclination angle θ2. The electrode 202 and the electrode 212 are arranged adjacent to each other in the longitudinal direction L of the arm.

A central electrode arrangement spot 232 is provided at the center of the electrode arrangement surface 100a, and five electrodes 203, 204, 205, 208, 213 are arranged at the central electrode arrangement spot 232. Of five electrodes 203, 204, 205, 208, 213, the electrode 203 is a third electrode, the electrode 204 is a fourth electrode, and the electrode 205 is a fifth electrode. These three electrodes 203, 204, 205 extend in the longitudinal direction of the arm, and are arranged substantially in parallel with each other in the circumferential direction of the arm. Moreover, the electrode 208 is an eighth electrode. The electrode 208 is an electrode elongated in the circumferential direction of the arm. The electrode 213 is a ground electrode commonly used for the opposing electrodes 203, 204, 205, 208.

The electrode 203, the electrode 204, and the electrode 205 are electrodes configured to separately provide stimuli to different muscles of the forearm according to a channel, and the electrode 213 is commonly used as a ground electrode. Three electrodes 203, 204, 205 are arranged in the circumferential direction H of the arm, and the electrode 213 as the common ground electrode arranged adjacent to three electrodes 203, 204, 205 in the longitudinal direction L is a rectangular electrode elongated in the circumferential direction H of the arm.

The electrode 208 is a rectangular electrode elongated, adjacent to the electrode 213, in the circumferential direction H of the arm. The electrode 213 is also used as the ground potential of the electrode 208. Note that the electrode 208 is an electrode used as backup. The electrode 208 is elongated in the circumferential direction H of the arm, and therefore, stimuli can be simultaneously provided to multiple muscles of the arm.

A left electrode arrangement spot 233 is provided at a left portion 102 (on the right side in FIG. 2) of the electrode arrangement surface 100a, and four electrodes 206, 207, 216, 217 are arranged at the left electrode arrangement spot 233. Of four electrodes 206, 207, 216, 217, the electrode 206 is a sixth electrode, and the electrode 207 is a seventh electrode. Moreover, the electrode 216 is a ground electrode facing the electrode 206, and the electrode 217 is a ground electrode facing the electrode 207.

The electrode 206 and the electrode 216 are electrodes configured to provide stimuli to the muscles of the forearm, and are substantially rectangular electrodes arranged with these electrodes being inclined with respect to the circumferential direction H at the same angle θ1 as the inclination angle θ1 of the left portion 102.

The electrode 207 and the electrode 217 are electrodes configured to provide stimuli to the muscles of the forearm, and upon attachment, are arranged adjacent to each other in the longitudinal direction L of the arm.

The muscle displacement sensors 221, 222 are arranged at two spots in the vicinity of the right electrode arrangement spot 231 of the electrode arrangement surface 100a. The muscle displacement sensors 223, 224, 225, 226 are arranged at four spots in the vicinity of the central electrode arrangement spot 232 of the electrode arrangement surface 100a. The muscle displacement sensors 227, 228 are arranged at two spots in the vicinity of the left electrode arrangement spot 233 of the electrode arrangement surface 100a.

Eight muscle displacement sensors 221 to 228 are well-known photoreflectors. Each of these muscle displacement sensors includes an infrared light emission element 221a to 228a and an infrared light receiving element 221b to 228b (see FIG. 6), and is configured to detect a change in a distance from a muscle displacement sensor arrangement surface to a surface of the muscle of the arm. The infrared light emission elements 221a to 228a are, for example, near infrared LEDs, and the infrared light receiving elements 221b to 228b are, for example, phototransistors.

When the muscle contracts, the distance between the photoreflector and the surface portion of the muscle fluctuates due to a projection of a skin portion of the muscle. The photoreflector detects, by the phototransistor, the intensity of reflected near infrared light in association with such distance fluctuation. The near infrared light exhibits the property of penetrating a skin surface, and therefore, is suitable for detection of a projecting state of the muscle.

Note that a resin material (not shown) exhibiting adhesion is arranged at other spots of the electrode arrangement surface 100a than the right electrode arrangement spot 231, the central electrode arrangement spot 232, and the left electrode arrangement spot 233, and the adhesion of the resin material allows the electrode arrangement surface 100a to be attached in a state of being wound around the forearm.

[2. Attachment Example of Electrical Stimulation Device 100]

Figure 3A:
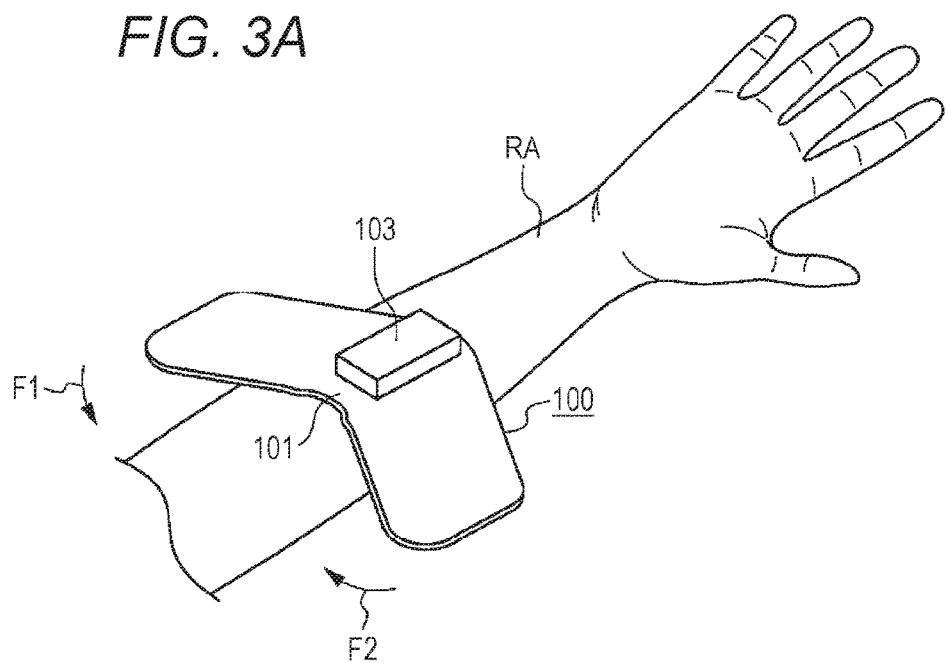
FIG. 3 is a view of a state right before and right after the electrical stimulation device is attached to a forearm.

FIG. 3A is a view of a state right before the electrical stimulation device 100 is attached to the forearm.

Figure 3B:
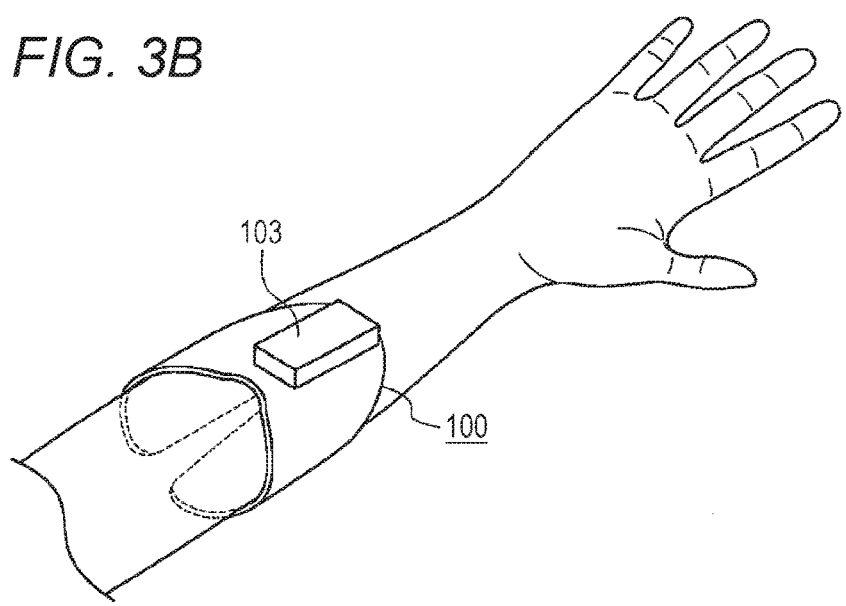

FIG. 3B is a view of a state right after the electrical stimulation device 100 has been attached to the forearm.

As illustrated in FIG. 3A, a center portion of the electrode arrangement surface 100a (FIG. 2) of the band 101 is in contact with a spot close to the wrist of the forearm RA of the right arm of the user. In this state, the palm is at such a position that the palm faces up as illustrated in FIG. 3A. Moreover, the circuit housing box 103 at the center of the substantially V-shaped band 101 faces a palm side.

Then, the user performs the process of winding both wings of the band 101 around the wrist as indicated by an arrow F1 and an arrow F2.

In this manner, the electrical stimulation device 100 is attached in a state of being wound around the forearm RA as illustrated in FIG. 3B. In this state, the adhesion of the adhesive resin material arranged on the electrode arrangement surface 100a maintains a winding state around the forearm RA.

Note that the winding state around the forearm RA only by the adhesion of the resin material is one example. For example, some kind of clip mechanism may be provided at both ends of the band 101 to hold these portions in an overlapping state.

As described above, the electrical stimulation device 100 is attached with the band 101 being wound around the forearm RA, and therefore, can be easily attached. Moreover, the band 101 is in the substantially V-shape. Thus, the user can easily recognize an attachment direction, and can reliably wear the electrical stimulation device 100 in a given direction as illustrated in FIG. 3B.

Note that the example where the electrical stimulation device 100 is attached to the right arm of the user is illustrated in FIG. 3, but the electrical stimulation device 100 may be attached to the left arm.

As illustrated in FIGS. 3A and 3B, the electrical stimulation device 100 according to the embodiment of the present invention is wound around the spot close to the wrist of the forearm RA of the user. However, a mark for fixing the electrical stimulation device 100 at a fixed position of the forearm RA of the user in this state is not provided at the forearm RA. That is, every time the user wears the electrical stimulation device 100 on the forearm RA, an attachment position is often slightly shifted. For this reason, every time the user wears the electrical stimulation device 100 on the forearm, a relative position relationship among the electrodes and the muscle displacement sensors provided on the electrode arrangement surface 100a of the electrical stimulation device 100 and the muscles of the arm of the user is shifted.

In response to such "shift," the present invention has been made for such a purpose that the electrical stimulation device 100 accurately grasps a correspondence among the electrodes and finger motion.

[Usage Pattern of Electrical Stimulation Device 100]

Figure 4:
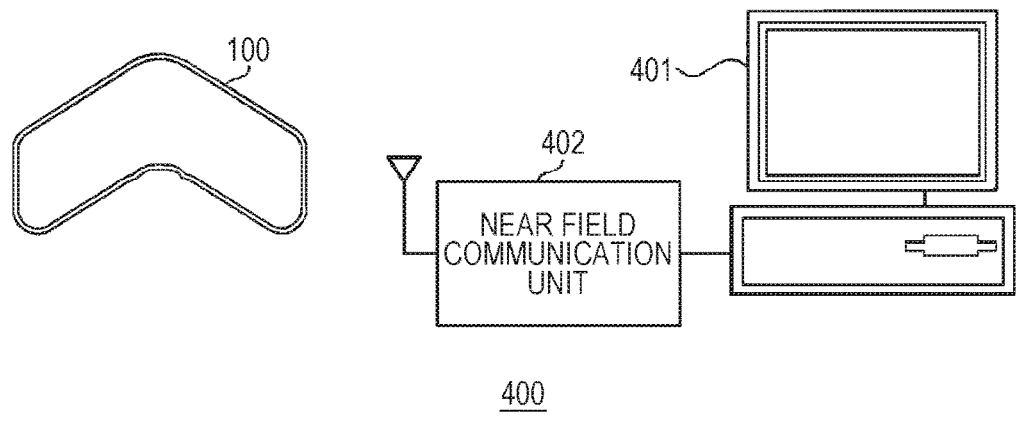
FIG. 4 is a schematic view of an electrical stimulation system having the electrical stimulation device as one example of a usage pattern of the electrical stimulation device.

FIG. 4 is a schematic view of an electrical stimulation system 400 having the electrical stimulation device 100 as one example of a usage pattern of the electrical stimulation device 100.

The electrical stimulation device 100 has a near field communication function such as the Bluetooth (registered trademark) as described later. By, e.g., a personal computer including a near field communication function equivalent to that of the electrical stimulation device 100 or connection of peripheral equipment providing a near field communication function with a personal computer, the electrical stimulation device 100 establishes bidirectional communication with the personal computer by near field communication. Hereinafter, the personal computer configured to establish bidirectional communication with the electrical stimulation device 100 by near field communication will be referred to as a "host 401." In FIG. 4, a near field communication unit 402 is connected to the host 401, and bidirectional communication with the electrical stimulation device 100 is established.

An application program such as a shooter game is in operation in the host 401. According to user's operation for the application program, the host 401 transmits a command for providing an electrical stimulus to a predetermined muscle of the user to the electrical stimulation device 100 via near field communication. Based on the electrical stimulation command received from the host 401, the electrical stimulation device 100 provides the electrical stimulus to the desired muscle of the user.

Moreover, the electrical stimulation device 100 transmits, as digital data, information on displacement of the muscle of the arm of the user to the host 401 by the above-described muscle displacement sensors.

Driving of the muscle displacement sensors includes driving for light emission from the infrared LEDs, accompanied by relatively-great power consumption. For this reason, for acquiring the arm muscle displacement information from the electrical stimulation device 100 with the minimum power consumption, the application program of the host 401 transmits, according to the state thereof, a command for driving and stopping the muscle displacement sensors to the electrical stimulation device 100. That is, the host 401 does not allow the electrical stimulation device 100 to drive the muscle displacement sensors until a situation where the application program needs the user arm muscle displacement information is brought during execution of the application program. At the time of bringing the situation where the application program needs the user arm muscle displacement information, a command for driving the muscle displacement sensors is transmitted from the host 401 to the electrical stimulation device 100. In response to the command from the host 401, the electrical stimulation device 100 drives the muscle displacement sensors to acquire the arm muscle displacement information.

At the time of terminating acquisition of the necessary arm muscle displacement information by the application program, the host 401 transmits a command to the electrical stimulation device 100 to stop driving of the muscle displacement sensors. In response to the command from the host 401, the electrical stimulation device 100 stops driving of the muscle displacement sensors.

That is, the electrical stimulation device 100 functions as an input device configured to collect the user arm muscle displacement information for the host 401 and an output device configured to provide displacement to the arm muscles. It can be also said that the electrical stimulation device 100 is a terminal for the host 401 and/or the application program.

As described with reference to FIG. 2, eight electrodes are, excluding the around electrodes, present on the electrode arrangement surface 100a of the electrical stimulation device 100. On the other hand, a human hand has five fingers. This is because the number of electrodes exceeding the number of fingers, i.e., five fingers, is provided to absorb an individual difference in a person's arm thickness only by the single electrical stimulation device 100. That is, eight electrodes include those not corresponding to motion of the fingers. Depending on the state of attachment of the electrical stimulation device 100 to the user's arm, the shift of a muscle position relative to the electrode often occurs due to shift of the attachment position. The number of electrodes exceeding the number of fingers, i.e., five fingers, is preferably provided so that the electrodes can be provided corresponding to the muscles even when such shift occurs.

For accurately operating the electrical stimulation device 100, a correspondence among the muscles for actually moving the fingers, the electrodes, and the muscle displacement sensors needs to be clarified by a calibration process.

For this reason, there are, as operation modes of the electrical stimulation device 100 according to the embodiment of the present invention, two types of operation modes including a normal mode for operation as the terminal for the application program and a calibration mode for carrying out the calibration process of clarifying the correspondence among the muscles for actually moving the fingers, the electrodes, and the muscle displacement sensors.

Note that in a block diagram for later describing software functions, the normal mode and the calibration mode will be separately described. The present invention is an invention specifically relating to the calibration mode of these modes.

[Hardware Configuration of Host 401]

Figure 5:
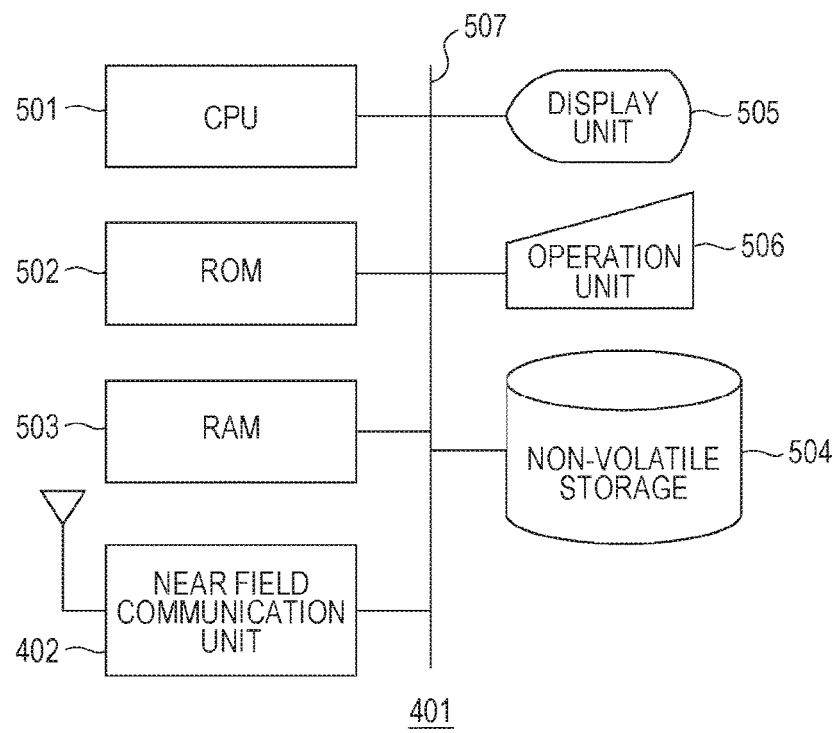
FIG. 5 is a block diagram of a hardware configuration of a host.

FIG. 5 is a block diagram of a hardware configuration of the host 401.

The host 401 including the typical personal computer as described above includes a CPU 501, a ROM 502, a RAM 503, a nonvolatile storage 504, a display unit 505, an operation unit 506, and the near field communication unit 402, these units being connected to a bus 507. The near field communication unit 402 is hardware for performing near field communication with the electrical stimulation device 100. The non-volatile storage 504 stores an OS and the application program for operating the personal computer as the host 401 of the electrical stimulation device 100.

[Hardware Configuration of Electrical Stimulation Device 100]

Figure 6:
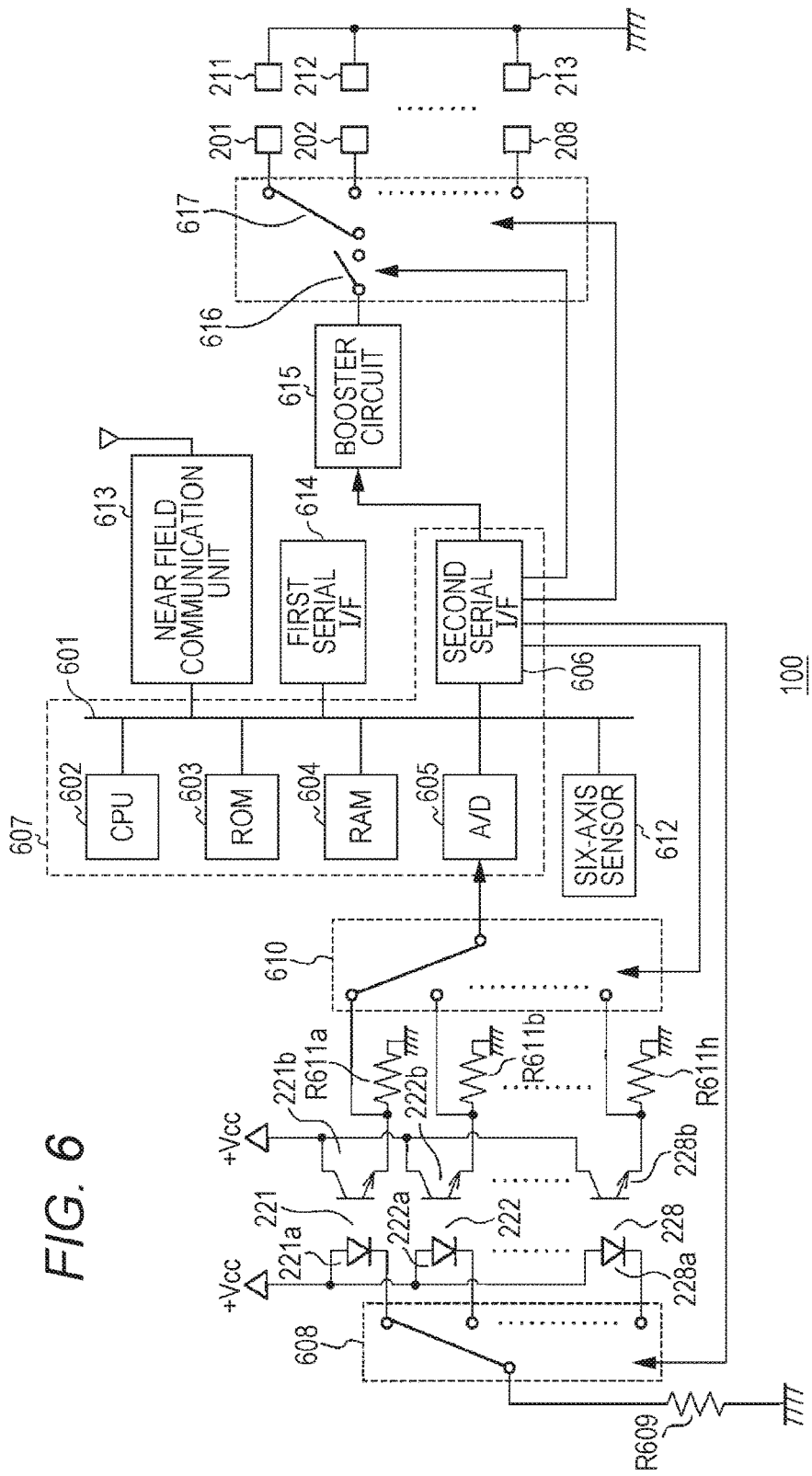
FIG. 6 is a block diagram of a hardware configuration of the electrical stimulation device.

FIG. 6 is a block diagram of a hardware configuration of the electrical stimulation device 100. A CPU 602, a ROM 603, a RAM 604, an A/D converter 605, and a second serial interface 606 (in FIG. 6, abbreviated as a "second serial I/F") connected to a bus 601 form a well-known one-chip microcomputer 607.

Anodes of the infrared light emission elements 221a, 222a, ..., 228a as the infrared LEDs forming the muscle displacement sensors 221, 222, ..., 228 are connected to a power source voltage node +Vcc. Cathodes of the infrared light emission elements 221a, 222a, ..., 228a are connected to one end of a current-limiting resistor R609 via a first multiplexor 608. The other end of the current-limiting resistor R609 is connected to ground.

Collectors of the infrared light receiving elements 221b, 222b, ..., 228b as the phototransistors forming the muscle displacement sensors 221, 222, ..., 228 are connected to the power source voltage node +Vcc. Emitters of the infrared light receiving elements 221b, 222b, . . . , 228b are connected to the A/D converter 605 via a second multiplexor 610, and are connected to ground via resistors R611a, R611b, . . . , R611h.

The first multiplexor 608 and the second multiplexor 610 are switchably controlled at regular intervals in response to a control signal from the second serial interface 606. In this manner, eight voltage signals of the muscle displacement sensors 221, 222, . . . , 228 are input to the A/D converter 605 in a time-division manner. The first multiplexor 608 and the second multiplexor 610 can be collectively referred to as a "sensor multiplexor" configured to select one of the multiple muscle displacement sensors 221, 222, . . . , 228.

A well-known six-axis sensor 612 and a near field communication unit 613 are also connected to the bus 601 of the one-chip microcomputer 607, and orientation information and acceleration information output from the six-axis sensor 612 are, together with information on eight muscle displacement sensors 221, 222, . . . , 228 as obtained via the A/D converter 605, transmitted to the host 401 via the near field communication unit 613.

A first serial interface 614 (in FIG. 6, abbreviated as a "first serial I/F") is further connected to the bus 601 of the one-chip microcomputer 607. Note that the first serial interface 614 supplies power to the not-shown storage battery, and therefore, is used for updating the firmware stored in the ROM 603.

A booster circuit 615 including a well-known choke coil, a well-known capacitor, and a well-known transistor switch is further connected to the second serial interface 606. A square-wave pulse signal with a voltage substantially equal to the power source voltage +Vcc is, with, e.g., 100 kHz, supplied to the booster circuit 615 from the second serial interface 606, This square-wave pulse signal performs ON/OFF control for the not-shown transistor switch in the booster circuit 615.

Then, the voltage of the square-wave pulse signal is increased to double by the booster circuit 615. An electrical stimulation voltage output from the booster circuit 615 is supplied to the electrodes 201, 202, . . . , 208 via a PWM switch 616 and a third multiplexor 617.

The PWM switch 616 is controlled by the second serial interface 606, thereby performing PWM modulation for the electrical stimulation voltage increased by the booster circuit 615. The duty ratio of the electrical stimulation voltage changes by PWM modulation, and therefore, the electrical stimulation voltage applied to the muscle is changed to a desired voltage. The third multiplexor 617 is also controlled via the second serial interface 606, Accordingly, the electrode specified by the command received from the host 401 via the near field communication unit 613 is selected, and the electrical stimulation voltage subjected to PWM modulation is applied to such an electrode.

It can be also said that the third multiplexor 617 is an electrode multiplexor configured to select one of the multiple electrodes 201, 202, . . . , 208.

[Software Functions of Electrical Stimulation Device 100 and Host 401 in Normal Mode]

Figure 7:
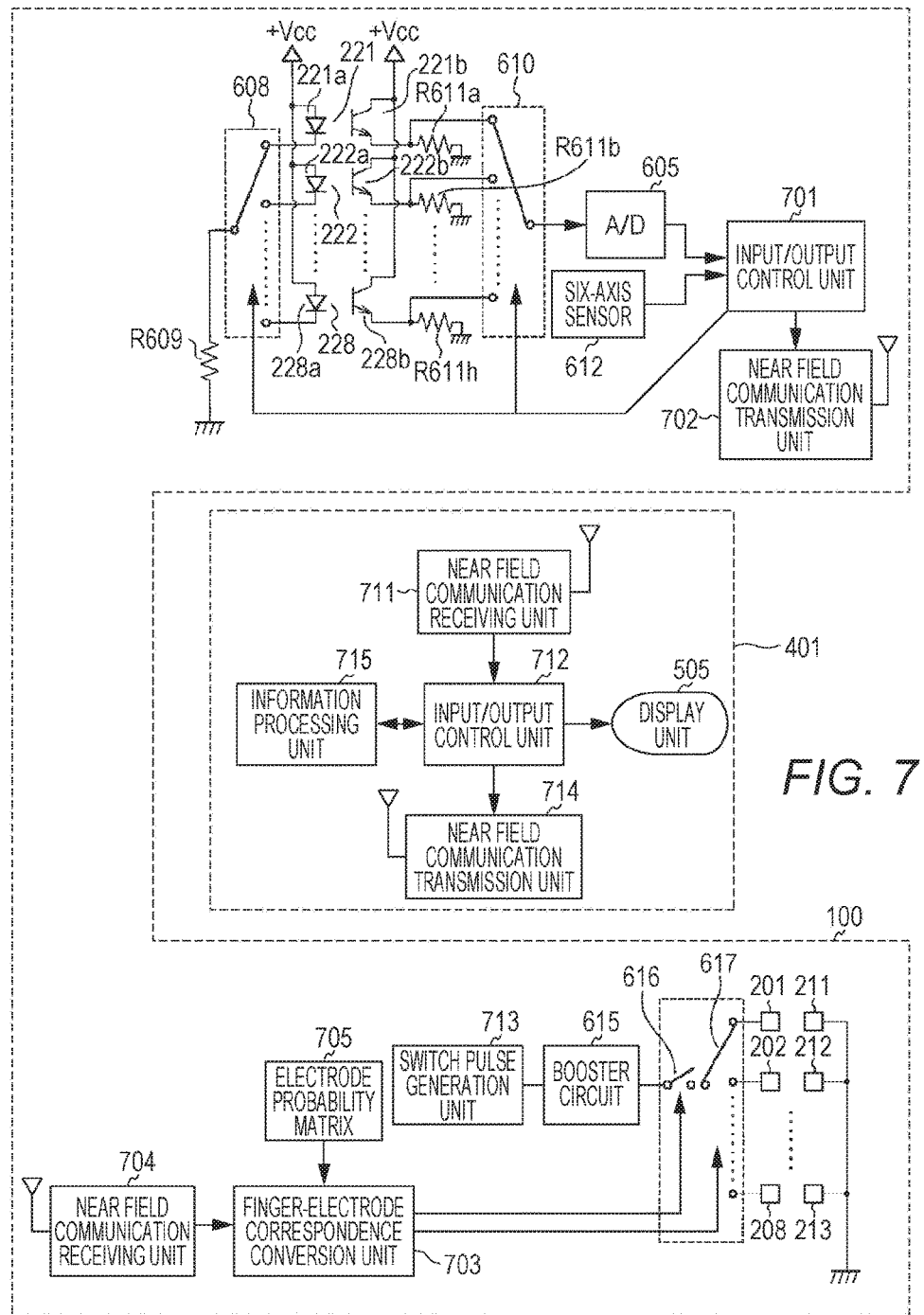
FIG. 7 is a block diagram of software functions of the electrical stimulation device and the host in a normal mode.

FIG. 7 is a block diagram of software functions of the electrical stimulation device 100 and the host 401 in the normal mode.

The electrical stimulation device 100 is an input/output terminal device having the function of transmitting, to the host 401, fluctuation in the user's arm muscles and the orientation and acceleration of the electrical stimulation device 100 itself and the function of providing the electrical stimuli to the muscles of the user's arm according to the command received from the host 401.

That is, analog signals output from eight muscle displacement sensors 221 to 228 are converted into the muscle displacement information by the A/D converter 605, and together with the orientation information and the acceleration information output from the six-axis sensor 612, are transmitted to the host 401 via an input/output control unit 701 and a near field communication transmission unit 702.

When receiving the muscle displacement information, the orientation information, and the acceleration information from the electrical stimulation device 100 via a near field communication receiving unit 711, the host 401 supplies these types of information to an input/output control unit 712. The input/output control unit 712 is configured to supply, after having received from the electrical stimulation device 100, the muscle displacement information, the orientation information, and the acceleration information to an information processing unit 715 as a predetermined application program such as a game and to output predetermined screen drawing information to the display unit 505 based on drawing information output from the information processing unit 715. Moreover, the input/output control unit 712 is configured to transmit electrical stimulation information output from the information processing unit 715 to the electrical stimulation device 100 via a near field communication transmission unit 714.

When receiving, via a near field communication receiving unit 704, the electrical stimulation execution command output from the host 401, a finger-electrode correspondence conversion unit 703 of the electrical stimulation device 100 refers to an electrode probability matrix 705 held in the RAM 604. Then, a finger number specified by the command is converted into an electrode number, and the PWM switch 616 and the third multiplexor 617 are controlled such that the electrical stimulation voltage is applied to a desired one of the electrodes 201 to 208.

Note that details of the electrode probability matrix 705 will be described later with reference to FIG. 9 and subsequent figures thereof.

Note that the input/output control unit 701 configured to control the operation timing of the first multiplexor 608 and the second multiplexor 610 for performing the operation of switching the muscle displacement sensors 221 to 228 and the finger-electrode correspondence conversion unit 703 configured to control the operation timing of the third multiplexor 617 for performing the operation of switching the electrodes are fully in asynchronous with each other. Thus, in FIG. 7, the input/output control unit 701 and the finger-electrode correspondence conversion unit 703 are illustrated as separate functional blocks.

[Software Functions of Electrical Stimulation Device 100 and Host 401 in Calibration Mode]

Figure 8:
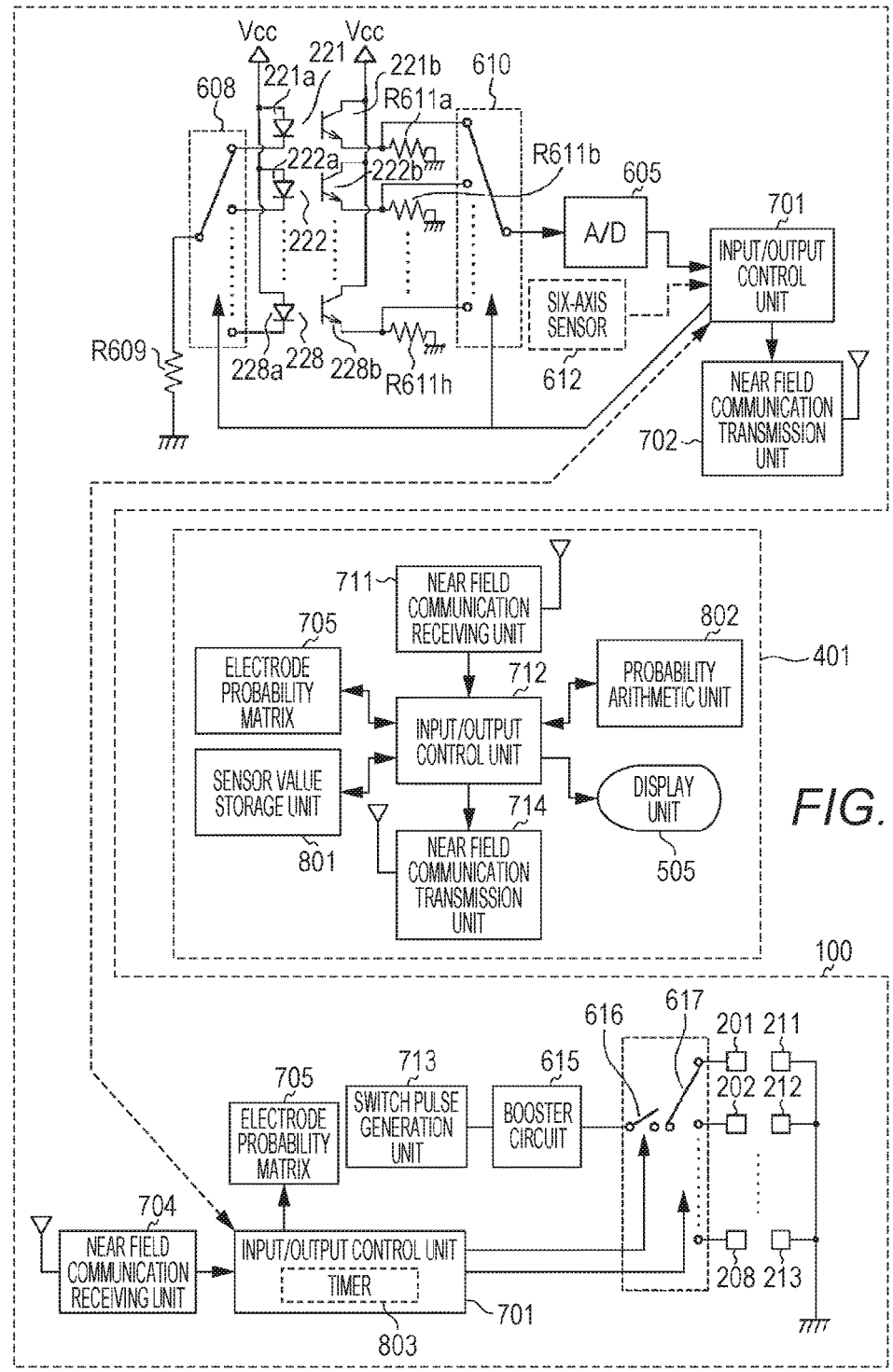
FIG. 8 is a block diagram of the software functions of the electrical stimulation device and the host in a calibration mode.

FIG. 8 is a block diagram of software functions of the electrical stimulation device 100 and the host 401 in the calibration mode.

Differences of the software functions of the electrical stimulation device 100 and the host 401 as illustrated in FIG. 8 from those of FIG. 7 are:

<1> the function of the six-axis sensor 612 unnecessary for the calibration mode is stopped;

<2> the input/output control unit 712 of the host 401 stores a sensor value in a sensor value storage unit 801 provided in the RAM 503 or the non-volatile storage 504 and produces or updates the electrode probability matrix 705 to transmit the electrode probability matrix 705 to the electrical stimulation device 100; and <3> the electrical stimulation device 100 provides, based on the command transmitted from the host 401, the electrical stimulus to the selected electrode to synchronously scan the muscle displacement sensors 221 to 228.

Specifically for <3>, the input/output control unit 701 of the electrical stimulation device 100 starts up a built-in timer 803 after the electrical stimulus has been provided to the electrode based on the command transmitted from the host 401. After a lapse of a predetermined time, the muscle displacement sensors 221 to 228 are scanned.

Meanwhile, based on information, which has been received from the electrical stimulation device 100, on the muscle displacement sensors 221 to 228, the input/output control unit 712 of the host 401 acquires an arithmetic result of a probability arithmetic unit 802 to produce or update the electrode probability matrix 705. Then, the produced or updated electrode probability matrix 705 is transmitted to the electrical stimulation device 100 via the near field communication transmission unit 714. Moreover, the input/output control unit 712 of the host 401 displays, during execution of the calibration mode, a progress in the calibration mode on the display unit 505 by a predetermined message, for example.

[Software Operation of Host 401 in Calibration Mode]

The electrode probability matrix 705 is matrix data indicating a correspondence among electrodes corresponding to the muscles for moving the user's fingers and finger motion. FIG. 17 illustrates one example of a generalized electrode probability matrix 705. The vertical axis (the row) of the electrode probability matrix 705 indicates an electrode, and the horizontal axis (the column) of the electrode probability matrix 705 indicates finger motion. A Bayesian posterior probability by Bayesian estimation is stored in each element.

In the normal mode, when receiving the command for moving a desired finger from the host 401, the finger-electrode correspondence conversion unit 703 of the electrical stimulation device 100 refers to the electrode probability matrix 705 based on finger information specified by the host 401. That is, the row of the electrode probability matrix 705 corresponding to the finger information and specified by the host 401 is referred. The probability is stored in each element forming such a row. The electrode corresponding to the element indicating the maximum probability among these elements is an electrode with the highest probability of moving the finger. As described above, the finger-electrode correspondence conversion unit 703 converts the finger specified by the host 401 into the electrode number, and based on such information, controls the third multiplexor 617.

When the electrical stimulation voltage is provided to a certain electrode, a predetermined muscle is stimulated, and the finger corresponding to such a muscle moves. Then, a certain muscle displacement sensor detects such muscle displacement, and the bent finger is determined with reference to correspondence data stored in the sensor value storage unit 801. That is, a relationship between finger motion and the electrode is in a one-to-one correspondence.

It has been, with reference to FIG. 2, described that eight electrodes other than the ground electrodes and eight muscle displacement sensors are provided on the electrode arrangement surface 100a of the electrical stimulation device 100. As described above, a reason why eight electrodes and eight muscle displacement sensors are provided for five fingers is that the individual difference in the person's arm thickness is absorbed only by the single electrical stimulation device 100. Thus, some of these electrodes do not correspond to finger motion. That is, for accurately operating the electrical stimulation device 100, the correspondence among, actual finger motion and the electrodes needs to be clarified by the calibration process.

Figure 9:
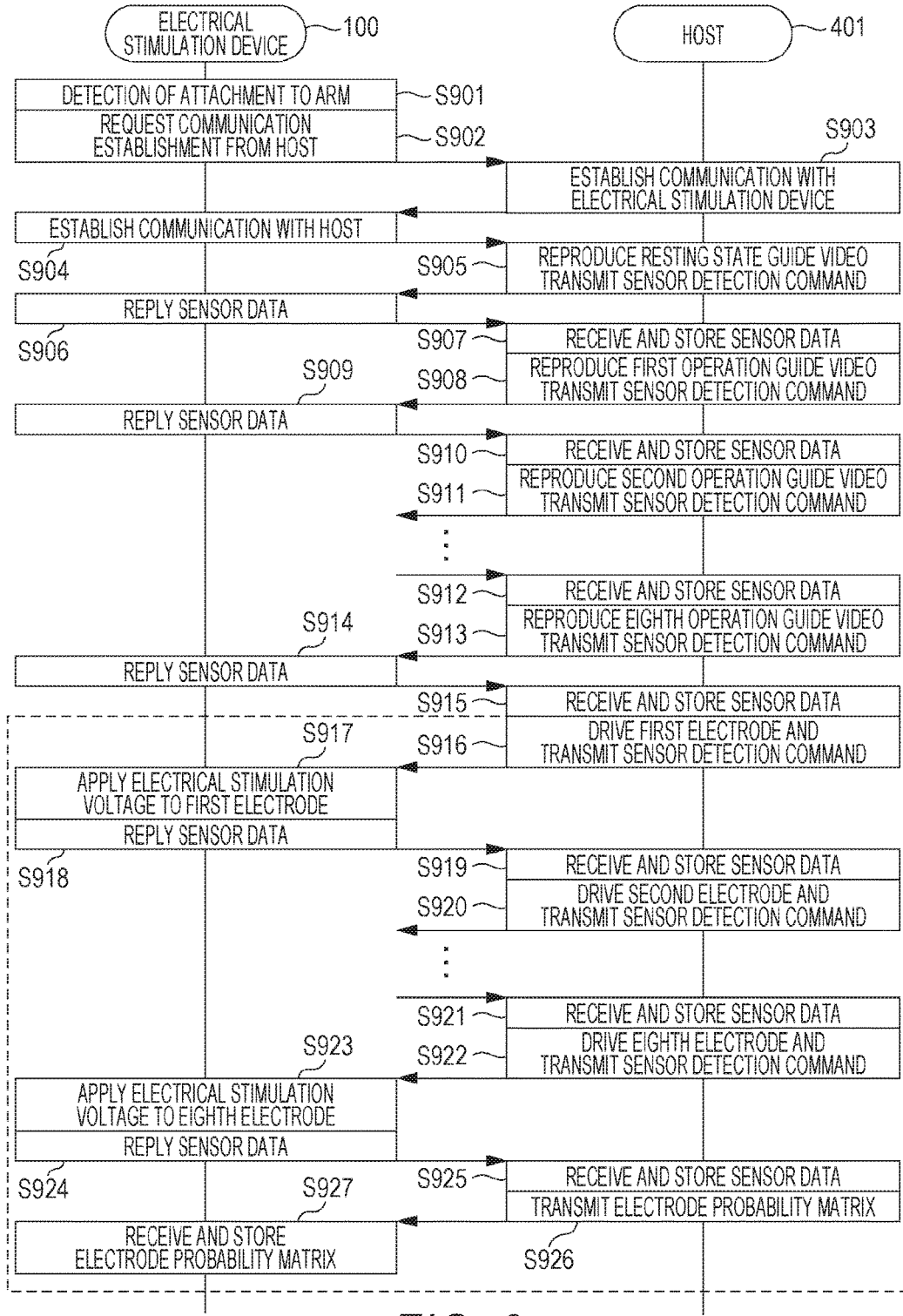
FIG. 9 is a time chart of the flow of calibration operation executed by the electrical stimulation device and the host in the calibration mode.

FIG. 9 is a time chart of the flow of calibration operation executed by the electrical stimulation device 100 and the host 401 in the calibration mode.

When the electrical stimulation device 100 is attached to the users arm, muscle displacement sensors detect that the skin of the user comes close to detection regions of the muscle displacement sensors. When it is detected that the electrical stimulation device 100 is attached to the user's arm (S901), the input/output control unit 701 of the electrical stimulation device 100 requests communication establishment from the host 401 via the near field communication unit 613 (S902). In response to the communication request from the electrical stimulation device 100, the host 401 replies a status message indicating communication establishment (S903). The electrical stimulation device 100 receives the status message from the host 401, and replies, to the host 401, a status message indicating that communication establishment has been recognized (S904).

When receiving the status message indicating recognition of communication establishment from the electrical stimulation device 100 via the near field communication receiving unit 704, the input/output control unit 712 of the host 401 starts the process of calibrating the muscle displacement sensors. First, video data named a "resting state guide video" stored in the non-volatile storage 504 of the host 401 is reproduced and displayed in the display unit 505. Then, a command for collecting data of the muscle displacement sensors is transmitted to the electrical stimulation device 100 (S905). The "resting state guide video" is video data displaying an illustration of a relaxing hand when the electrical stimulation device 100 is attached to a forearm and a message of "Please wait while relaxing your hand." When receiving the command from the host 401, the electrical stimulation device 100 replies the data of all muscle displacement sensors to the host 401 (S906). The muscle displacement sensor value at this point is a muscle displacement sensor value in a state in which the user's fingers are relaxed, and is a reference value for detecting whether or not the muscle is relaxed.

When receiving the data of eight muscle displacement sensors from the electrical stimulation device 100, the host 401 stores such data as "resting state data" (S907). Next, video data named a "first operation guide video" stored in the non-volatile storage 504 of the host 401 is reproduced, and is displayed on the display unit 505. Then, the command for collecting the data of the muscle displacement sensors is transmitted to the electrical stimulation device 100 (S908). The "first operation guide video" is video data displaying an illustration of the hand with a thumb being bent when the electrical stimulation device 100 is attached to the forearm and a message of "Please wait while bending your thumb." When receiving the command from the host 401, the electrical stimulation device 100 replies the data of all muscle displacement sensors to the host 401 (S909). The muscle displacement sensor value at this point is a muscle displacement sensor value in a state in which the user's thumb is not relaxed.

When receiving the data of eight muscle displacement sensors from the electrical stimulation device 100, the host 401 stores such data as "first operation state data" (S910). Next, video data named a "second operation guide video" stored in the non-volatile storage 504 of the host 401 is reproduced, and is displayed on the display unit 505. Then, the command for collecting the data of the muscle displacement sensors is transmitted to the electrical stimulation device 100 (S911). The "second operation guide video" is video data displaying an illustration of the hand with the index finger being bent when the electrical stimulation device 100 is attached to the forearm and a message of "Please wait while bending your index finger."

After the step S911, operation corresponding to the steps S908, S909, S910 is, starting from the step S908, performed eight times in total. At this point, the video data reproduced by the host 401 and the data received from the electrical stimulation device 100 by the host 401 and stored in the sensor value storage unit 801 are as follows:

"First Operation Guide Video": operation guide in the state in which the thumb is bent, and the first operation state data is stored;

"Second Operation Guide Video": operation guide in the state in which the index finger is bent, and the second operation state data is stored;

"Third Operation Guide Video": operation guide in a state in which the middle finger is bent, and third operation state data is stored;

"Fourth Operation Guide Video": operation guide in a state in which the ring finger or the little finger is bent, and fourth operation state data is stored;

"Fifth Operation Guide Video": operation guide in a state (palmar flexion) in which the wrist is bent toward the direction of the palm with the hand extending straight, and fifth operation state data is stored;

"Sixth Operation Guide Video": operation guide in a state (dorsal flexion) in which the wrist is bent toward the direction of the backhand with the hand extending straight, and sixth operation state data is stored;

"Seventh Operation Guide Video": operation guide in a state (radial flexion) in which the wrist is bent toward the direction of the thumb with the hand extending straight, and seventh operation state data is stored; and "Eighth Operation Guide Video": operation guide in a state (ulnar flexion) in which the wrist is bent toward the direction of the little finger with e hand extending straight, and eighth operation state data is stored.

When receiving the data of eight muscle displacement sensors from the electrical stimulation device 100, the host 401 stores such data as the "seventh operation state data" (S912). Next, the video data named the "eighth operation guide video" stored in the non-volatile storage 504 of the host 401 is reproduced, and is displayed on the display unit 505. Then, the command for collecting the data of the muscle displacement sensors is transmitted to the electrical stimulation device 100 (S913). The "eighth operation guide video" is video data displaying an illustration of the hand in the state in which the wrist is bent toward the direction of the little finger (ulnar flexion) with the hand extending straight when the electrical stimulation device 100 is attached to the forearm and a message of "Please wait while extending your hand straight and bending your wrist toward the direction of the little finger." When receiving the command from the host 401, the electrical stimulation device 100 replies the data of all muscle displacement sensors to the host 401 (S914). The muscle displacement sensor value at this point is a muscle displacement sensor value in the ulnar flexion state in which the user bends the wrists toward the direction of the little finger.

When receiving the data of the muscle displacement sensors from the electrical stimulation device 100, the host 401 stores such data as the "eighth operation state data" (S915).

As described above, the host 401 grasps a correspondence between fluctuation in the muscle displacement sensor value and finger motion through the step S905 to the step S915.

When the step S915 ends, the input/output control unit 712 of the host 401 calculates a relative value of each muscle displacement sensor. Specifically, a first reference value according to the thumb bending state is obtained in such a manner that the resting state data is subtracted from the first operation state data. A second reference value according to the index finger bending state is obtained in such a manner that the resting state data is subtracted from the second operation state data. Similarly, a third reference value according to the middle finger bending state, a fourth reference value according to the ring or little finger bending state, a fifth reference value according to the palmar flexion state, a sixth reference value according to the dorsal flexion state, a seventh reference value according to the radial flexion state, and an eighth reference value according to the ulnar flexion state are obtained. These first to eighth reference values form a group of the relative values of eight muscle displacement sensors. The input/output control unit 712 of the host 401 stores these first to eighth reference values in the sensor value storage unit 801.

Next, the input/output control unit 712 of the host 401 multiplies these first to eighth reference values by a predetermined ratio to obtain thresholds. The ratio to be multiplied by the first to eighth reference values is herein 50%, for example. The input/output control unit 712 of the host 401 also stores these thresholds in the sensor value storage unit 801.

The intensity of reflected light detected by the phototransistor of the muscle displacement sensor greatly varies according to factors (uncertainties) such as the states of the user's skin and muscle opposing the muscle displacement sensor and a relative position relationship between the muscle displacement sensor and the user's skin. For this reason, the input/output control unit 712 of the host 401 stores, in the sensor value storage unit 801, the muscle displacement sensor values in a state in which the user's fingers are mostly relaxed and in a state in which a user's specific finger is bent, and calculates a difference between these values. Since the obtained reference values are the relative variations of the muscle displacement sensors, influence of the uncertainties can be eliminated.

The A/D converter 605 configured to digitalize the analog signal output from the muscle displacement sensor is, for example, a 10-bit unsigned integer (0 to 1023). It has been found that when the inventors produce the electrical stimulation device 100 on trial, the relative variation obtained from the muscle displacement sensor having detected displacement of the muscle is around 300 to 900.

After a later-described step S916, the resting state data is subtracted from the data of each muscle displacement sensor received by the host 401 from the electrical stimulation device 100, and in this manner such data of the muscle displacement sensor is converted into the relative value of the muscle displacement sensor. Then, an input/output device compares the relative value of the muscle displacement sensor with the threshold to determine whether or not a predetermined finger has moved.

The host 401 having grasped the correspondence between fluctuation in the muscle displacement sensor value and finger motion through the steps S905 to S915 subsequently begins the process of grasping the correspondence among the electrodes and finger motion.

The input/output control unit 712 of the host 401 transmits, to the electrical stimulation device 100, a command for collecting the data of the muscle displacement sensors after the electrical stimulation voltage has been applied to the first electrode (S916). When receiving the command from the host 401, the electrical stimulation device 100 applies the electrical stimulation voltage to the first electrode (S917), and after a lapse of a predetermined time, collects the data of the muscle displacement sensors to return such data to the host 401 (S918).

When receiving the data of the muscle displacement sensors from the electrical stimulation device 100, the input/output control unit 712 of the host 401 stores, as sensor value data in the first electrode, the data in the sensor value storage unit 801 (S919). Next, the input/output control unit 712 of the host 401 transmits, to the electrical stimulation device 100, a command for collecting the data of the muscle displacement sensors after the electrical stimulation voltage has been applied to the second electrode (S920).

After the step S920, operation corresponding to the steps S916, S917, S918, S919 is, starting from the step S916, performed eight times in total. At this point, the command transmitted to the electrical stimulation device 100 by the host 401 and the data received by the host 401 from the electrical stimulation device 100 and stored in the sensor value storage unit 801 are as follows:
the command for collecting the data of the muscle displacement sensors after the electrical stimulation voltage has been applied to the first electrode: the sensor value data in the first electrode is stored;
the command for collecting the data of the muscle displacement sensors after the electrical stimulation voltage has been applied to the second electrode: sensor value data in the second electrode is stored;
a command for collecting the data of the muscle displacement sensors after the electrical stimulation voltage has been applied to the third electrode: sensor value data in the third electrode is stored;
a command for collecting the data of the muscle displacement sensors after the electrical stimulation voltage has been applied to the fourth electrode: sensor value data in the fourth electrode is stored;
a command for collecting the data of the muscle displacement sensors after the electrical stimulation voltage has been applied to the fifth electrode: sensor value data in the fifth electrode is stored;
a command for collecting the data of the muscle displacement sensors after the electrical stimulation voltage has been applied to the sixth electrode: sensor value data in the sixth electrode is stored;
a command for collecting the data of the muscle displacement sensors after the electrical stimulation voltage has been applied to the seventh electrode: sensor value data in the seventh electrode is stored; and
a command for collecting the data of the muscle displacement sensors after the electrical stimulation voltage has been applied to the eighth electrode: sensor value data in the eighth electrode is stored.

When receiving the data of the muscle displacement sensors from the electrical stimulation device 100, the input/output control unit 712 of the host 401 stores, as the sensor value data in the seventh electrode, the data in the sensor value storage unit 801 (S921). Next, the input/output control unit 712 of the host 401 transmits, to the electrical stimulation device 100, the command for collecting the data of the muscle displacement sensors after the electrical stimulation voltage has been applied to the eighth electrode (S922).

When receiving the command from the host 401, the electrical stimulation device 100 applies the electrical stimulation voltage to the eighth electrode (S923), and after a lapse of the predetermined time, collects the data of the muscle displacement sensors to return such data to the host 401 (S924).

When receiving the data of the muscle displacement sensors from the electrical stimulation device 100, the input/output control unit 712 of the host 401 stores, as the sensor value data in the eighth electrode, the data in the sensor value storage unit 801 (S925). Next, the input/output control unit 712 of the host 401 generates or updates the first to eighth operation state data corresponding to motion of each finger as stored in a series of operation from the steps S905 to S915 and the sensor value data in each electrode as stored in a series of operation from the steps S916 to S925.

Note that as a result of execution of a first learning mode (described later with reference to FIG. 10 and subsequent figures), if the electrode probability matrix 705 is present in the host 401, such updating is also performed for the electrode probability matrix 705 through the probability arithmetic unit 802, The input/output control unit 712 of the host 401 transmits the generated or updated electrode probability matrix 705 to the electrical stimulation device 100 (S926). Then, the electrical stimulation device 100 stores, in the RAM 503, the electrode probability matrix 705 received from the host 401 (S927), and ends a series of processing.

The steps S905 to S915 of FIG. 9 are a muscle displacement sensor calibration mode for clarifying a correlation among the muscle displacement sensors and finger motion. The input/output control unit 712 of the host 401 executes the muscle displacement sensor calibration mode, and in this manner, it is clarified from the data obtained from the muscle displacement sensors 221 to 228 which finger is currently moving.

The steps S916 to S927 surrounded by a dashed line in FIG. 9 are the learning mode for clarifying a correlation among the electrodes and finger motion by production and updating of the electrode probability matrix 705. The input/output control unit 712 of the host 401 executes the learning mode, and in this manner, it is clarified to which electrode of the electrodes 201 to 208 the electrical stimulation voltage needs to be applied to move a desired finger.

That is, the calibration mode includes the muscle displacement sensor calibration mode and the learning mode. Hereinafter, the learning mode will be described with reference to FIG. 10.

Figure 10:
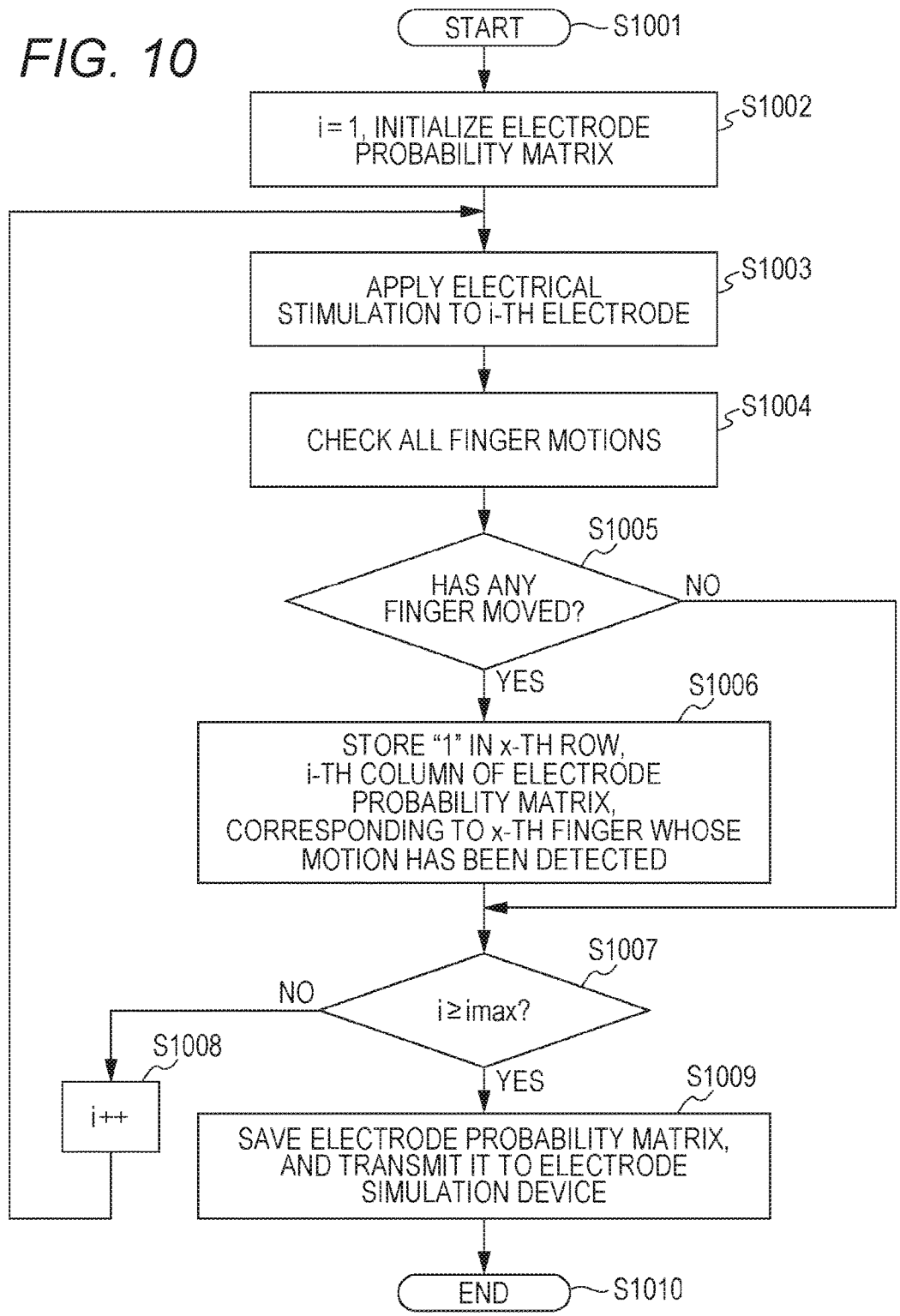
FIG. 10 is a flowchart for describing the flow of operation in an initial learning mode executed by the host when a user wears the electrical stimulation device on the arm for the first time.

FIG. 10 is a flowchart of the flow of operation of the initial learning mode executed by the host 401 when the user wears the electrical stimulation device 100 for the first time.

When the processing begins (S1001), the input/output control unit 712 of the host 401 first initializes a counter variable i to 1, and initializes all elements of the electrode probability matrix 705 to "0" (S1002).

Subsequent processing is executed in a loop. The input/output control unit 712 of the host 401 transmits, to the electrical stimulation device 100, the command for collecting the data of the muscle displacement sensors after the electrical stimulation voltage has been applied to an i-th electrode (S1003). Then, the input/output control unit 712 of the host 401 calculates the difference value from the data of the muscle displacement sensors received from the electrical stimulation device 100 to compare such a value with the threshold, thereby checking whether or not finger motion occurs (S1004) In a case where it is detail tined that any finger has moved by the electrical stimulus by the i-th electrode (YES at S1005), the input/output control unit 712 of the host 401 stores "1" in the element of the electrode probability matrix 705 in an x-th row corresponding to the x-th finger whose motion has been detected and an i-th column corresponding to the i-th electrode (S1006).

After the step S1006 has been executed or in a case where it is, at the step S1005, determined that any finger is not moved by the electrical stimulus by the i-th electrode (NO at S1005), the input/output control unit 712 of the host 401 whether or not the counter variable i reaches the maximum value of i, i.e., the total number of electrodes. In a case where the counter variable i does not reach the total number of electrodes (NO at S1007), the input/output control unit 712 of the host 401 increments the counter variable i by one (S1008), and repeats the processing again from the step S1003.

At the step S1007, in a case where the counter variable i reaches the total number of electrodes (YES at S1007), the input/output control unit 712 of the host 401 saves the produced electrode probability matrix 705 in the non-volatile storage 504, and transmits the electrode probability matrix 705 to the electrical stimulation device 100 (S1009). Then, the input/output control unit 712 of the host 401 ends a series of processing (S1010).

Subsequently, operation of the step S1003 will be additionally described.

Figure 11:
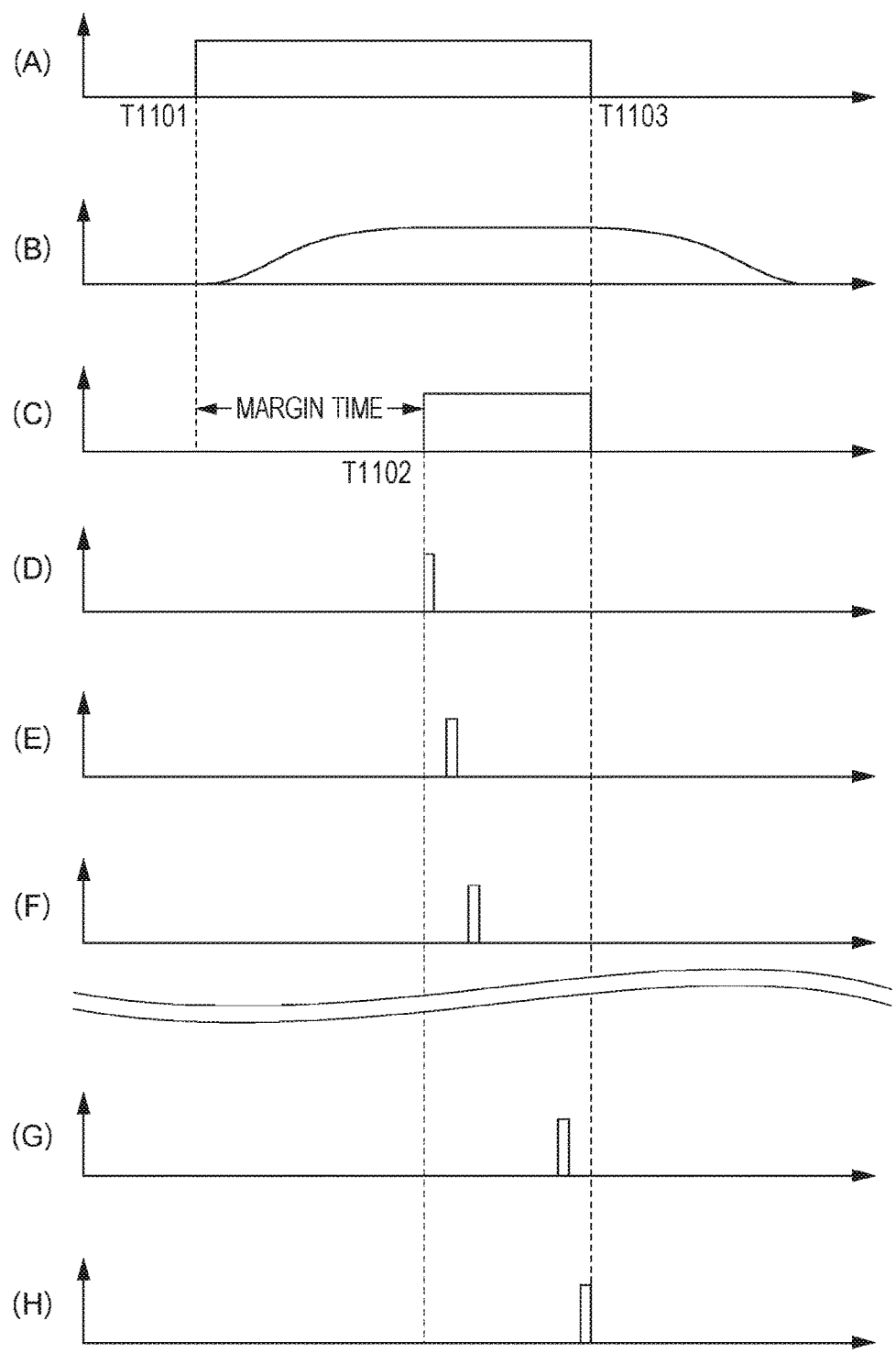
FIG. 11 is a time chart for describing an electric stimulus, a muscle contraction state, and muscle displacement sensor operation.

FIG. 11 is a time chart for describing the electrical stimulus, a muscle contraction state, and muscle displacement sensor operation.

Beginning at the top, in FIG. 11, (A) is the electrical stimulus applied to the electrode, (B) is the muscle contraction state, (C) is a gate signal indicating an operation period of the muscle displacement sensor in the input/output control unit 712, (D) is an operation period of the first muscle displacement sensor, (E) is an operation period of the second muscle displacement sensor, (F) is an operation period of the third muscle displacement sensor, (G) is an operation period of the seventh muscle displacement sensor, and (H) is an operation period of the eighth muscle displacement sensor. Only for (B) the muscle contraction state, the vertical axis represents the amount of displacement in muscle contraction. For other items, the vertical axis represents a logical value.

When the electrical stimulus is applied to the electrode at a time point T1101, the muscle starts contracting. From a time point T1102 at which muscle contraction becomes stable, the gate signal shows true of the logic. In response, scanning of the muscle displacement sensors begins. A time necessary for data collection from a single muscle displacement sensor is elapsed within about several msec to about several tens of msec. At a time point T1103 at which scanning for all of the muscle displacement sensors 221 to 228 ends, the logic of the gate signal is inverted to false. At the same time, application of the electrical stimulation voltage to the electrode also ends.

The operation of applying the electrical stimulation voltage to the electrode to scan the muscle displacement sensors 221 to 228 as illustrated in FIG. 11 is executed for all of eight electrodes.

A human muscle contracts when receiving an electrical stimulation voltage from the outside through an electrode. It takes about 0.1 seconds until the muscle contracts to a predetermined contraction amount and becomes stable after application of the electrical stimulation voltage. In the electrical stimulation device 100 according to the embodiment of the present invention, a margin time of 0.2 seconds is provided in expectation of a further margin. The margin time is a time until the time point T1102 at which muscle contraction becomes stable after the time point T1101 at which the electrical stimulation voltage is applied in FIG. 11.

Next, the electrode probability matrix 705 produced by the processing from the steps S1003 to S1008 will be described.

FIG. 12A is a view for describing a matrix indicating finger motion in response to the electrical stimulus. Hereinafter, such a matrix will be referred to as a "finger behavior matrix."

FIG. 12B is a view of the procedure of selecting an effective electrical stimulus from the finger behavior matrix.

FIG. 12C is a view for describing a matrix indicating a result of selection of the effective electrical stimulus from the finger behavior matrix. Such a matrix will be referred to as a "flag matrix."

FIG. 12D is a view of the electrode probability matrix 705 generated from the flag matrix.

At the step S1004, the input/output control unit 712 calculates the difference values for the muscle displacement sensors. Then, the difference values, which correspond to finger motion, for the muscle displacement sensors are derived. In a case where only a single muscle displacement sensor corresponds to certain finger motion, the difference value is directly employed. In a case where a combination of two or more muscle displacement sensors corresponds to certain finger motion, the average of the difference values for the muscle displacement sensors is employed. In this manner, numeric values illustrated in FIG. 12A are stored as elements of the finger behavior matrix.

Beginning at the top, the rows of the finger behavior matrix illustrated in FIGS. 12A and 12B, the rows of the flag matrix illustrated in FIG. 12C, and the rows of the electrode probability matrix 705 illustrated in FIG. 12D are as follows:
the first row: the state in which the thumb is bent, i.e., the thumb bending state;
the second row: the state in which the index finger is bent, i.e., the index finger bending state;
the third row: the state in which the middle finger is bent, i.e., the middle finger bending state;
the fourth row: the state in which the ring finger or the little finger is bent, i.e., the ring or little finger bending state;
the fifth row: the state (palmar flexion) in which the wrist is bent toward the direction of the palm with the hand extending straight, i.e., a wrist palmar flexion state;
the sixth row: the state (dorsal flexion) in which the wrist is bent toward the direction of the backhand with the hand extending straight, i.e., a wrist dorsal flexion state;
the seventh row: the state (radial flexion) in which the wrist is bent toward the direction of the thumb with the hand extending straight, i.e., a wrist radial flexion state; and
the eighth row: the state (ulnar flexion) in which the wrist is bent toward the direction of the little finger with the hand extending straight, i.e., a wrist ulnar flexion state.

The columns of the finger behavior matrix illustrated in FIGS. 12A and 12B, the columns of the flag matrix illustrated in FIG. 12C, and the columns of the electrode probability matrix 705 illustrated in FIG. 12D are, in the order from the left to the right, first to eighth electrical stimuli.

Next, the procedure of determining whether or not the finger has moved at the step S1004 of FIG. 10 will be described.

Focusing on the element in the first row and the first column to the element in the eighth row and the first column in the finger behavior matrix illustrated in FIG. 12B, elements of "595 115 92 0 0 0 0 0" are formed in the order from the top. Of these elements in this column, the element showing the maximum value is "595" in the first row and the first column. This value is stored in a maximum value array 1201. The maximum value array 1201 is an array for storing the maximum value in each column.

The position of the element "595" is (1, 1) of the finger behavior matrix, and such a row (the first row) corresponds to the thumb bending state. Thus, it is determined whether or not the value "595" exceeds the threshold for the thumb bending state. As a result of determination, it is determined that the value exceeds the threshold. Thus, the element in the first row and the first column in the finger behavior matrix is taken as effective, and true of the logic is stored in a flag array 1202. In FIG. 12B, such an element is represented by a white circle.

As described above, the maximum value is selected for each row in the finger behavior matrix, and is stored in the maximum value array 1201. Then, such a value is compared with the threshold in finger movement to which the element belongs based on the position of the element. As a result of comparison, when the maximum value is a value equal to or greater than the threshold, true of the logic is stored in the flag array 1202. Then, the element at the same position in the flag matrix as the position of the element of the maximum value array 1201 corresponding to true of the logic in the flag array 1202 is taken as true of the logic. This is the flag matrix of FIG. 12C.

The element with true of the logic in the flag matrix has a probability of 100% (=1). This is the electrode probability matrix 705 of FIG. 12D.

The electrode probability matrix 705 is a matrix indicating which finger to be moved and the probability of moving of the finger when the electrical stimulation voltage is provided to a certain electrode. The probability stored as the element of the electrode probability matrix 705 is a posterior probability by, e.g., Bayesian estimation. That is, production of the electrode probability matrix 705 in the flowchart of FIG. 10 is initial learning in Bayesian estimation.

At the point of time of execution of the flowchart of FIG. 10, the processing is still in initial learning. Thus, only any of 0 or 1 is present. These values fluctuate in a second learning mode or later as described below.

Figure 13:
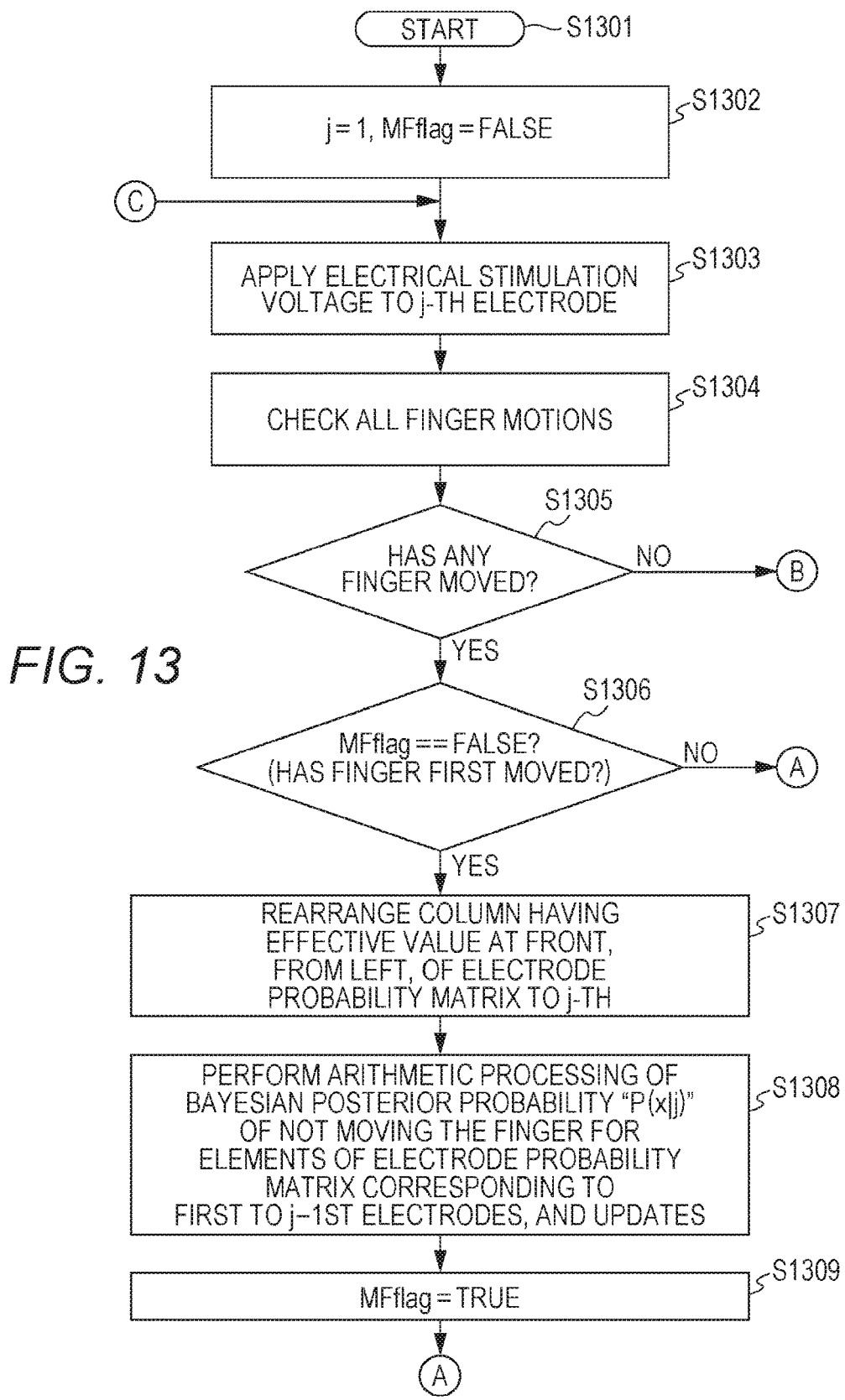
FIG. 13 is a flowchart for describing the flow of operation in a second learning mode or later executed by the host when the user wears the electrical stimulation device for the second time or later.
Figure 14:
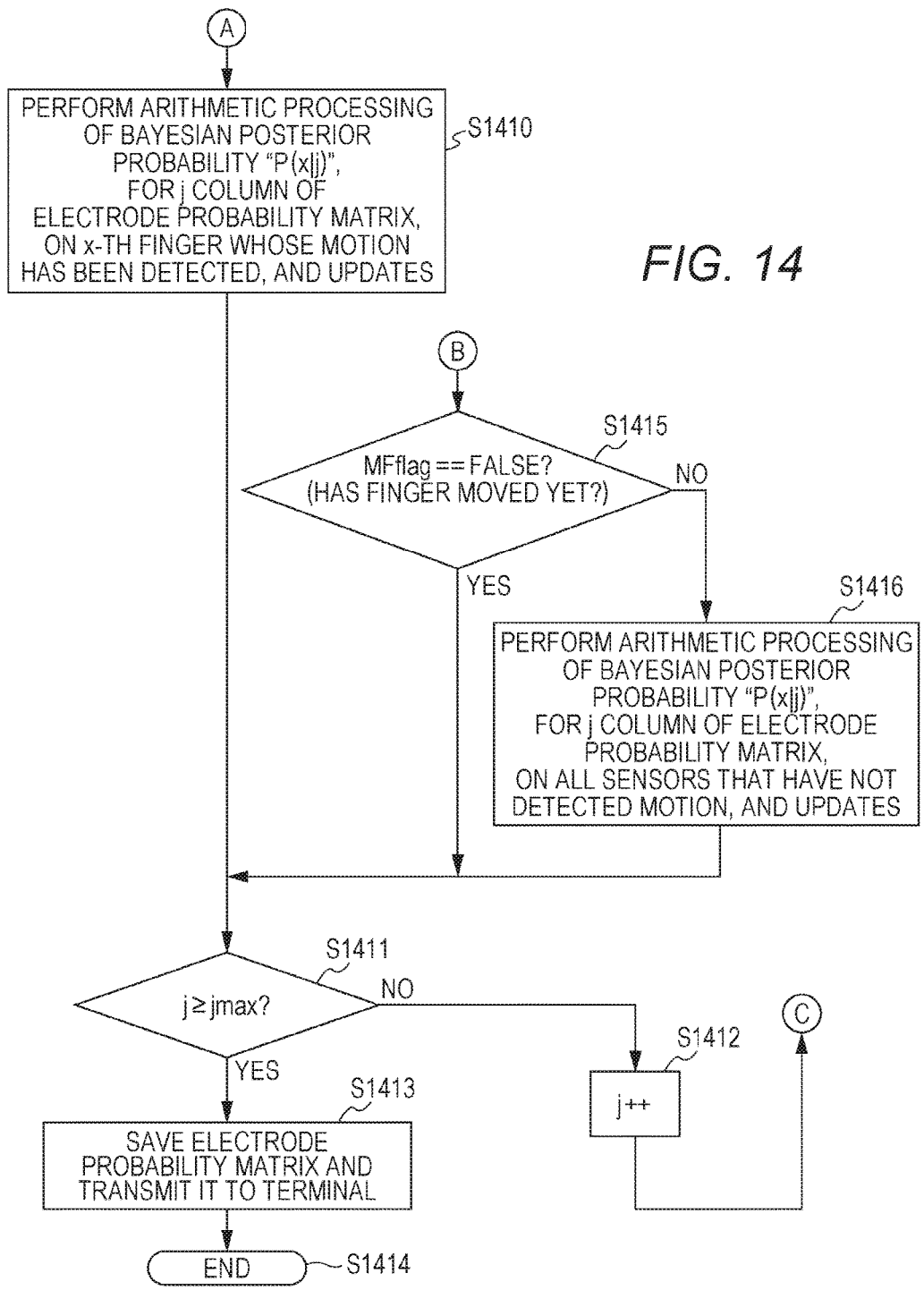
FIG. 14 is a flowchart for describing the flow of operation in the second learning mode or later executed by the host when the user wears the electrical stimulation device for the second time or later.

FIGS. 13 and 14 are flowcharts of the flow of operation of the second learning mode or later executed by the host 401 when the user wears the electrical stimulation device 100 for the second time or later.

When the processing begins (S130, the input/output control unit 712 of the host 401 first initializes a counter variable j to 1, and initializes a flag variable MFflag to false of the logic (S1302). The flag variable MFflag is a flag for recording occurrence of a state in which the finger is moved by the electrical stimulus.

Subsequent processing is executed in a loop. The input/output control unit 712 transmits, to the electrical stimulation device 100, the command for collecting the data of the muscle displacement sensors after the electrical stimulation voltage has been applied to a j-th electrode (S1303). Then, the input/output control unit 712 calculates the difference value from the data of the muscle displacement sensors from the electrical stimulation device 100 to compare such a value with the threshold, thereby checking whether or not finger motion occurs (S1304). The steps S1303 and S1304 have the same processing contents as those of the steps S1003 and S1004 of FIG. 10.

If it is determined that any finger is moved by the electrical stimulus by the j-th electrode (YES at S1305), the input/output control unit 712 subsequently checks whether or not the flag variable MFflag is false of the logic, "whether or not the finger has first moved at this point of time." If it is determined that the finger has first moved at this point of time (YES at S1306), the electrode probability matrix 705 saved in the non-volatile storage 504 of the host 401 is read out to the RAM 503, and the elements of the electrode probability matrix 705 on the RAM 503 are moved with the rows and/or the columns together (S1307). Since the elements of the electrode probability matrix 705 are moved as described above, a relative position relationship among the electrodes of the electrical stimulation device 100 currently attached to the arm of the user and the muscles is reflected in the electrode probability matrix 705.

Next, the input/output control unit 712 operates the probability arithmetic unit 802 to perform arithmetic processing of the Bayesian posterior probability "P(x|j)" of not moving the finger for the elements of the electrode probability matrix 705 corresponding to the first to j−1st electrodes, and updates the corresponding element of the electrode probability matrix 705 (S1308). Then, the flag variable MFflag is shifted to true of the logic (S1309), and the processing transitions to a step S1410 of FIG. 14. That is, after it has been determined, at the step S1305, that any finger has moved (YES at S1305), MFflag is shifted to true of the logic at the step S1306, and therefore, the processing transitions to the step S1410 of FIG. 14 without performing the processing of the steps S1307, S1308, and S1309.

Next, movement of the elements of the electrode probability matrix 705 at the step S1307 will be described in detail with reference to FIGS. 15A and 15B.

Figure 15A:
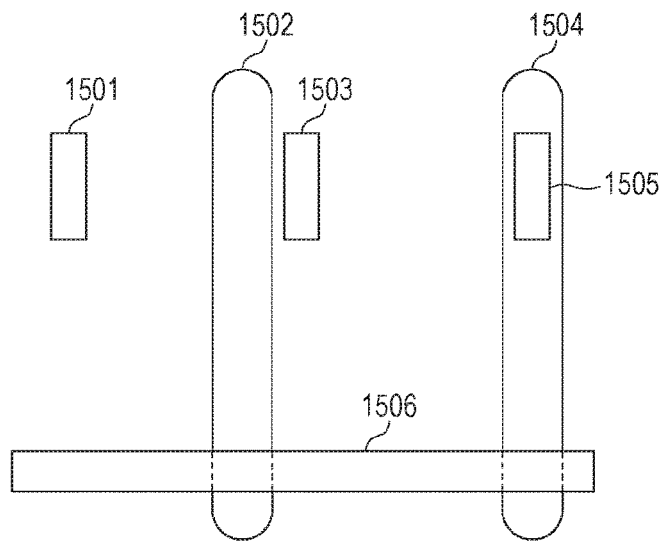
FIG. 15 is a schematic view for describing an arrangement relationship among arm muscles and electrodes when the user wears the electrical stimulation device on the arm for the first time, and a schematic view for describing the arrangement relationship among the arm muscles and the electrodes when the user again wears the electrical stimulation device on the arm.

FIG. 15A is a schematic view for describing an arrangement relationship among the arm muscles and the electrodes when the user wears the electrical stimulation device 100 on the arm for the first time.

Figure 15B:
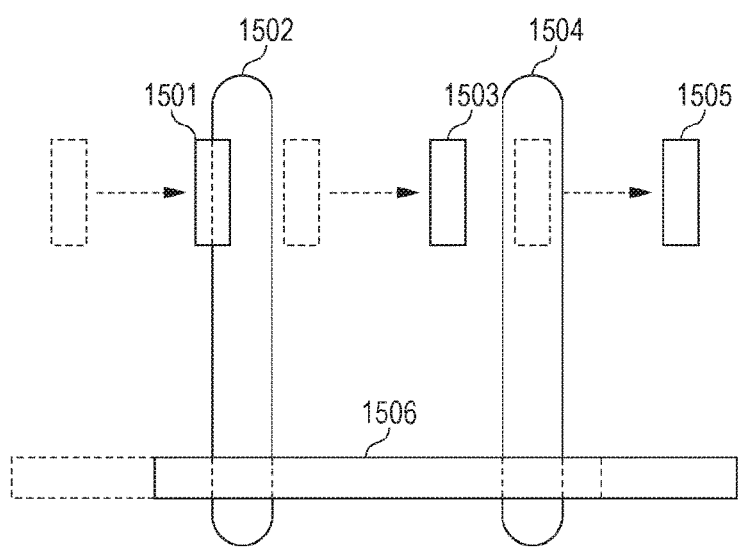

FIG. 15B is a schematic view for describing the arrangement relationship among the arm muscles and the electrodes when the user again wears the electrical stimulation device 100 on the arm.

In FIG. 15A, an electrode 1501 is apart from a muscle 1502. An electrode 1503 is close to the muscle 1502. An electrode 1505 is close to a muscle 1504. Note that an electrode 1506 is a ground electrode commonly used for the electrode 1501, the electrode 1503, and the electrode 1505.

In comparison between FIG. 15A and FIG. 15B, a relative position relationship between the user's arm and the electrode arrangement surface 100a of the electrical stimulation device 100 is shifted in FIG. 15B. Thus, the electrode 1501 is close to the muscle 1502, and the electrode 1503 is close to the muscle 1504. Moreover, the electrode 1505 is apart from the muscle 1504.

When the relative position relationship between the user's arm and the electrode arrangement surface 100a of the electrical stimulation device 100 is shifted as described above, arrangement of the electrodes opposing the muscles also changes. Such a phenomenon occurs as inconsistency among the elements of the finger behavior matrix and the elements of the flag matrix produced based on the finger behavior matrix. For this reason, the elements of the electrode probability matrix 705 stored in advance in the non-volatile storage 504 need to be adjusted to the detected finger behavior matrix.

FIG. 16A is an example of the finger behavior matrix produced in the second learning mode or later.

FIG. 16B is a virtual electrode probability matrix 705 produced based on the finger behavior matrix of FIG. 16A.

FIG. 16C is the electrode probability matrix 705 of FIG. 12D.

FIG. 16D is a matrix obtained by rearrangement of the electrode probability matrix 705 of FIG. 16C.

First, the electrode probability matrix 705 of FIG. 16C is, as described with reference to FIG. 12D, the matrix data produced in the first learning mode. On the other hand, the virtual electrode probability matrix 705 illustrated in FIG. 16B is matrix data produced in the second learning mode or later.

Only by comparison of the matrix data, it seems that the degree of shift of the relative position relationship (FIG. 16B) between the user's arm and the electrical stimulation device 100 in the second learning mode from the relative position relationship (FIG. 16C) between the user's arm and the electrical stimulation device 100 in the first learning mode is not noticeable. However, focusing on the element, which indicates that the finger has moved, on the upper left side of the matrix data, a position shift between the position (P1603) of the element at the point of time of initial finger movement in the first learning mode and the position (P1601) of the element at the point of time of initial finger movement in the second learning mode is clearly shown. That is, the shift between the relative position relationship between the user's arm and the electrical stimulation device 100 at a previous use point and the relative position relationship between the user's arm and the electrical stimulation device 100 at a current point is clearly shown as an element position shift.

As described earlier, the electrode probability matrix 705 is the matrix data indicating, in teams of probability, the correlation among the electrodes and finger motion. The Bayesian posterior probability by Bayesian estimation is applied as the probability. However, if the shift between the relative position relationship between the user's arm and the electrical stimulation device 100 at the previous use point and the relative position relationship between the user's arm and the electrical stimulation device 100 at the current point remains in the electrode probability matrix 705 before Bayesian estimation, the accuracy of learning is significantly lowered. For this reason, the input/output control unit 712 of the host 401 interchanges, in association with the relative position relationship between the user's arm and the electrical stimulation device 100 at the current point, the row and column elements of the electrode probability matrix 705 read out from the non-volatile storage 504 and held in the RAM 503. In the case of FIG. 16C, the column of the electrode probability matrix 705 of FIG. 16C is shifted to the right by one such that the position (1, 1) of the element P1603 is at the same position as the position (1, 2) of the element P1601 of FIG. 16B. Accordingly, an element group A1604 of FIG. 16C is arranged at the same position as an element group A1602 of FIG. 16B, Then, an element group A1605 of FIG. 16C is shifted out in association with movement of the element group A1604, and is arranged in the blank first column of the electrode probability matrix 705 at a left end thereof. This is the electrode probability matrix 705 of FIG. 16D.

Note that the processing of the step S1308 is the processing of updating the element group A1605 in FIG. 16D.

For the processing of searching for the element indicating the effective electrical stimulus and positioned on the upper left side of the electrode probability matrix 705 at the step S1307 of FIG. 13, the electrode probability matrix 705 is, for the sake of simplicity, configured based on an assumption that motion of the finger with the smallest number first occurs when the electrical stimulation voltage is sequentially applied to the electrodes. Note that this is for the sake of convenience, and therefore, the element of the electrode probability matrix 705 corresponding to finger motion first detected after the electrical stimulation voltage has been sequentially applied to the electrodes may be referred.

Note that in a case where the initially-moved finger is not in the thumb bending state at the step S1306 of FIG. 13, any electrode is not in the thumb bending state in the current relative position relationship between the user's arm and the electrical stimulation device 100. That is, arrangement of the electrodes fails to bend the thumb. In this case, the element in the same row of the electrode probability matrix 705 corresponding to the initially-moved finger is referred. That is, the first row indicating the thumb bending state of the electrode probability matrix 705 is ignored. The electrode probability matrix 705 is rearranged only in units of columns, but is not rearranged in units of rows.

Referring back to FIGS. 13 and 14, the flowchart will be continuously described.

After the step S1309 or at the step S1306, in the case where the flag variable MFflag is true of the logic (NO at S1306), the processing transitions to the processing of FIG. 14.

As illustrated in FIG. 14, the input/output control unit 712 operates the probability arithmetic unit 802 to perform arithmetic processing of the Bayesian posterior probability "$P(x|j)$" of moving the finger for the element indicating that the finger was moved among the elements of the electrode probability matrix 705 corresponding to the j-th electrode. Moreover, for the element indicating that the finger was not moved, arithmetic processing is performed to obtain the Bayesian posterior probability "$P(x|j)$" of not moving the finger, and the corresponding element of the electrode probability matrix 705 is updated (S1410).

Then, the input/output control unit 712 checks whether or not the counter variable j reaches the maximum value of j, i.e., the total number of electrodes. In a case where the counter variable j does not reach the total number of electrodes (NO at S1411) the input/output control unit 712 increments the counter variable j by one (S1412), and the processing is repeated again from the step S1303.

In a case where the counter variable j reaches, at the step S1411, the total number of electrodes (YES at S1411), the input/output control unit 712 saves the produced electrode probability matrix 705 in the non-volatile storage 504 to transmit the electrode probability matrix 705 to the electrical stimulation device 100 (S1413), and ends a series of processing (S1414).

Referring back to FIG. 13, in a case where any finger does not move at the step S1305 (NO at S1305), the input/output control unit 712 subsequently checks whether or not the flag variable MFflag is false of the logic, i.e., whether or not the finger does not move yet at this point (S1415). In a case where the finger does not move yet (YES at S1415), checking of the counter variable j at the step S1411 is performed without doing anything.

At the step S1415, when the flag variable MFflag is true of the logic, i.e., the finger has already moved at this point (NO at S1415), the input/output control unit 712 operates the probability arithmetic unit 802 to perform the Bayesian posterior probability "$P(x|j)$" of not moving the finger for all elements of the electrode probability matrix 705 corresponding to the j-th electrode, and updates the corresponding element of the electrode probability matrix 705 (S1416). Then, checking of the counter variable j at the step S1411 is performed.

Determination at the step S1415 is the processing of determining whether or not rearrangement of the electrode probability matrix 705 at the step S1307 has been performed. As long as the electrode probability matrix 705 indicating the relative position relationship between the user's arm and the electrical stimulation device 100 at the previous use point is not adjusted to the relative position relationship between the user's arm and the electrical stimulation device 100 at the current point, learning by Bayesian estimation cannot be accurately carried out for the electrode probability matrix 705. Thus, Bayesian estimation arithmetic processing is not performed until the processing of the step S1307 is completed (YES at S1415), but is performed after the processing of the step S1307 has been completed (S1308, S1410, NO of S1415 to S1416).

The electrical stimulation device 100 according to the embodiment of the present invention includes eight muscle displacement sensors and eight electrodes, but the number of muscle displacement sensors and the number of electrodes are not necessarily eight. Rather, a greater number of muscle displacement sensors and a greater number of electrodes result in finer detection of the muscle contraction state and finer muscle contraction control.

FIG. 17 is a view of one example of the generalized electrode probability matrix 705. Every time the user repeatedly uses the electrical stimulation device 100, the electrical stimulation device 100 is repeatedly attached/detached to/from the user's arm. That is, every time the electrical stimulation device 100 is attached/detached to/from the user's arm, the learning mode is executed. When the learning mode is repeatedly executed, a correlation between a certain electrode and finger motion is fixed as a result. For the x rows and the j columns, the Bayesian posterior probability "P(x|j)" is stored in each element of the electrode probability matrix 705.

The embodiment of the present invention described above is applicable as follows.

(1) It is assumed that a single electrical stimulation device 100 is installed per household. An arm thickness varies among a father, a mother, and a child. Thus, in a case where the single electrical stimulation device 100 is shared by multiple users, a user authentication function is preferably provided at the host 401, and the electrode probability matrix 705 is preferably linked to a user ID.

Any type of user authentication may be employed as long as a unit having the function of uniquely identifying the user. For example, not only general password authentication using a keyboard but also biometric authentication such as fingerprints, veins, and irises can be utilized. It is easy to use a biometric authentication unit using the fingerprint or the vein when such a unit is housed in the circuit housing box 103 of the electrical stimulation device 100.

Moreover, when this user authentication function is integrated with a user authentication function of the information processing unit 715 as the application program, user authentication of the electrical stimulation device 100 and user authentication of the application program can be unified. Thus, better usability can be expected. In this case, the user ID is linked to user data of the information processing unit 715 and the electrode probability matrix 705 of the electrical stimulation device 100.

That is, a device driver program of the electrical stimulation device 100 installed in the host 401 contains the user authentication function. The application program utilizes the user authentication function of the device driver program so that sharing of the electrical stimulation device 100 by multiple users and unification of user authentication can be realized.

(2) In the flowcharts illustrated in FIGS. 10, 13, and 14, the data of the muscle displacement sensors is taken after the electrical stimulus has been provided to the electrode, and then, finger motion is checked. Thereafter, the determination and learning processing sequentially proceed. However, the electrical stimulus may be first provided to the electrode, and then, the process of taking the data of the muscle displacement sensors may be executed for all electrodes to produce the finger behavior matrix in advance. Thereafter, the determination and learning processing may be performed. Needless to say, the step S1307 of FIG. 13 is also essential in this case.

(3) In the electrical stimulation device 100 according to the embodiment of the present invention, Bayesian estimation is employed as a learning algorithm. However, the learning algorithm is not limited to above. For example, other supervised learning algorithms such as a support vector machine may be used.

In the present embodiment, the electrical stimulation device 100 and the electrical stimulation system 400 have been disclosed.

For clarifying a correlation between electrical stimulation by the electrodes and finger motion, the electrode probability matrix 705 configured such that the Bayesian posterior probability indicating finger motion corresponding to the electrode is described as the element is produced in the host 401, and is transferred to the electrical stimulation device 100. In the second learning mode or later, for adjusting the previous electrode probability matrix 705 to a current state of attachment of the electrical stimulation device 100 to the user's arm, the position of the element positioned on the upper left side of the electrode probability matrix 705 and indicating that the finger has moved is compared, and as necessary, the columns of the electrode probability matrix 705 are rearranged.

The electrical stimulation device 100 and the host 401 are configured as described above. Thus, the electrical stimulation device 100 and the electrical stimulation system 400 can be realized, the device and the system being configured so that even in the state of attachment to one arm of the user, the correspondence among finger motion and the electrodes can be clarified in a short amount of time and an intended finger can be driven at high accuracy with very few erroneous operation.

The embodiment of the present invention has been described above, but the present invention is not limited to the above-described embodiment. Other variations and applications are included without departing from the gist of the present invention described in the claims.

For example, the above-described embodiment is for specifically describing detailed device and system configurations to clearly describe the present invention, and is not necessarily limited to that including all of the described configurations. Moreover, some of configurations of a certain embodiment may be replaced with configurations of other embodiments. Further, configurations of other embodiments may be added to a certain embodiment. In addition, for some of configurations of each embodiment, addition/elimination/replacement of other configurations is available.

Part or the entirety of each configuration, function, processing unit, etc. as described above may be implemented in hardware by designing using an integrated circuit, for example. Moreover, each configuration, function, etc. as described above may be implemented in software for interpreting and executing a program for implementing each function by a processor. Information for implementing each function, such as a program, a table, and a file, can be held in a recording medium such as a memory, a hard drive, a volatile or non-volatile storage such as a solid state drive (SSD), an IC card, or an optical disk.

Control and information lines assumed as necessary for description are illustrated, and all control and information lines for a product are not necessarily illustrated. It may be assumed that almost all configurations are actually connected to each other.

DESCRIPTION OF REFERENCE SIGNS 100 electrical stimulation device
101 band
102 left portion
103 circuit housing box
104 first serial interface terminal
150 arithmetic processing unit
201, 202, 203, 204, 205, 206, 207, 208, 211, 212, 213, 216 electrode
217 electrode
221, 223, 227 muscle displacement sensor
231 right electrode arrangement spot
232 central electrode arrangement spot
233 left electrode arrangement spot
400 electrical stimulation system
401 host
402 near field communication unit
501 CPU
502 ROM
503 RAM
504 non-volatile storage
505 display unit
506 operation unit
507 bus
601 bus
602 CPU
603 ROM
604 RAM
605 A/D converter
606 second serial interface
607 one-chip microcomputer
608 first multiplexor
610 second multiplexor
612 six-axis sensor
613 near field communication unit
614 first serial interface
615 booster circuit
616 PWM switch
617 third multiplexor
701 input/output control unit
702 near field communication transmission unit
703 finger-electrode correspondence conversion unit
704 near field communication receiving unit
705 electrode probability matrix
711 near field communication receiving unit
712 input/output control unit
715 information processing unit
714 near field communication transmission unit
801 sensor value storage unit
802 probability arithmetic unit
803 timer
1201 maximum value array
1202 flag array

The invention claimed is:

1. An electrical stimulation system comprising:
an electrical stimulation device; and
a host configured to transmit, to the electrical stimulation device, a command for moving a finger,
wherein the electrical stimulation device includes
a band adapted to be wound around an arm of a user,
multiple muscle displacement sensors arranged on one surface of the band and configured to detect muscle displacement of the arm of the user,
a sensor multiplexor configured to select one of the multiple muscle displacement sensors,
multiple electrodes arranged adjacent to the multiple muscle displacement sensors on the surface of the band on which the multiple muscle displacement sensors are arranged,
an electrode multiplexor configured to select one of the multiple electrodes,
a near field communication receiving unit configured to receive the command for moving the finger from the host,
a near field communication transmission unit configured to convert a signal obtained from each muscle displacement sensor and relating to the muscle displacement of the arm of the user into digital data to transmit the digital data to the host,
an electrode probability matrix configured such that a correspondence among finger motion and the multiple electrodes is described in terms of probability, and
a finger-electrode correspondence conversion unit configured to specify, based on the command for moving the finger, an electrode with a maximum probability from the electrode probability matrix and to control the electrode multiplexor to select the specified electrode, and
the host includes
a near field communication receiving unit configured to receive the data of each muscle displacement sensor from the electrical stimulation device,
the electrode probability matrix,
an input/output control unit configured to update an element of the electrode probability matrix after a shift of a current relative position relationship between the arm of the user and the electrical stimulation device has been detected to rearrange the element of the electrode probability matrix after the data of each muscle displacement sensor has been converted into the finger motion of the user, and
a near field communication transmission unit configured to transmit the updated electrode probability matrix to the electrical stimulation device.

2. The electrical stimulation system according to claim 1, wherein
the host further includes
a probability arithmetic unit configured to calculate a posterior probability based on a learning algorithm to update an element of the electrode probability matrix.

* * * * *